(12) United States Patent
Langella et al.

(10) Patent No.: US 11,717,543 B2
(45) Date of Patent: Aug. 8, 2023

(54) FAECALIBACTERIUM PRAUSNITZII STRAINS FOR TREATING AND PREVENTING GASTROINTESTINAL PAIN

(71) Applicants: INSTITUT NATIONAL DE LA RECHERCHE AGRONOMIQUE (INRA), Paris (FR); INSTITUT NATIONAL DE LA SANTE ET DE LA RECHERCHE MEDICALE (INSERM), Paris (FR); UNIVERSITE PIERRE ET MARIE CURIE (PARIS 6), Paris (FR); ASSISTANCE PUBLIQUE - HOPITAUX DE PARIS (APHP), Paris (FR); ECOLE D'INGENIEURS DE PURPAN, Toulouse (FR)

(72) Inventors: Philippe Langella, Velizy-Villacoublay (FR); Sylvie Miquel, Beaumont (FR); Rebeca Martin Rosique, Jouy en Josas (FR); Luis Bermudez Humaran, Jouy en Josas (FR); Muriel Thomas, Igny (FR); Harry Sokol, Paris (FR); Frédéric Carvalho, Clermont-Ferrand (FR); Vassilia Theodorou, Portet Sure Garonne (FR)

(73) Assignees: INSTITUT NATIONAL DE LA RECHERCHE AGRONOMIQUE (INRA), Paris (FR); INSTITUT NATIONAL DE LA SANTE ET DE LA RECHERCHE MEDICALE, Paris (FR); UNIVERSITE PIERRE ET MARIE CURIE (PARIS 6), Paris (FR); ASSISTANCE PUBLIQUE—HOPITAUX DE PARIS, Paris (FR); ECOLE D'INGENIEURS DE PURPAN, Toulous (FR)

( * ) Notice: Subject to any disclaimer, the term of this patent is extended or adjusted under 35 U.S.C. 154(b) by 298 days.

(21) Appl. No.: 16/907,381

(22) Filed: Jun. 22, 2020

(65) Prior Publication Data
US 2020/0316138 A1  Oct. 8, 2020

Related U.S. Application Data

(62) Division of application No. 15/524,808, filed as application No. PCT/EP2015/076572 on Nov. 13, 2015, now abandoned.

(30) Foreign Application Priority Data

Nov. 13, 2014 (EP) .................................. 14306803

(51) Int. Cl.
A61K 35/741 (2015.01)
A23L 33/135 (2016.01)
A61P 29/00 (2006.01)

(52) U.S. Cl.
CPC .......... *A61K 35/741* (2013.01); *A23L 33/135* (2016.08); *A61P 29/00* (2018.01)

(58) Field of Classification Search
None
See application file for complete search history.

(56) References Cited

FOREIGN PATENT DOCUMENTS

WO   WO-2014137211 A1 * 9/2014 ............. A23K 10/16

OTHER PUBLICATIONS

Langella ("Commensal Bacteria and Recombinant Lactic Acid Bacteria as Novel Probiotics for Human Intestinal Health", Vail d' Hebron Institut de Recerca (VHIR) Seminar and Conferences, Dec. 3, 2012, Barcelona, Spain Abstract further cited and provided) (Year: 2012).*

Delvaux ("Role of visceral sensitivity in the pathophysiology of irritable bowel syndrome" Gut, 2002, 51 (Supplemental I, 67-71). (Year: 2002).*

* cited by examiner

*Primary Examiner* — Robert J Yamasaki
*Assistant Examiner* — Charles Zoltan Constantine
(74) *Attorney, Agent, or Firm* — WCF IP

(57) ABSTRACT

The present invention relates to a bacterial strain of the *Faecalibacterium prausnitzii* species selected from a bacterial strain belonging to one of the phylogroups I, II and III, for use in the treatment and/or prevention of visceral abdominal pain in an individual.

The present invention also concerns compositions comprising said bacterial strains as well as specific strains as such.

5 Claims, 3 Drawing Sheets
Specification includes a Sequence Listing.

SEQUENCE LISTING

<160> NUMBER OF SEQ ID NOS: 18

<210> SEQ ID NO 1
<211> LENGTH: 1474
<212> TYPE: DNA
<213> ORGANISM: Faecalibacterium prausnitzii

<400> SEQUENCE: 1

```
agagtttgat cctggctcag gacgaacgct ggcggcgcgc ctaacacatg caagtcgaac      60
gagtgagaga gagcttgctt tctcgagcga gtggcgaacg ggtgagtaac gcgtgaggaa     120
cctgcctcaa agaggggggac aacagttgga aacgactgct aataccgcat aagcccacgg    180
ctcggcatcg agcagaggga aaaggagtga tccgctttga gatggcctcg cgtccgatta    240
gctagttggt gaggtaatgg cccaccaagg cgacgatcgg tagccggact gagaggttga    300
acggccacat tgggactgag acacggccca gactcctacg ggaggcagca gtggggaata    360
ttgcacaatg ggggaaaccc tgatgcagcg acgccgcgtg gaggaagaag gtcttcggat    420
tgtaaactcc tgttgttggg gaagataatg acggtaccca acaaggaagt gacggctaac    480
tacgtgccag cagccgcggt aaaacgtagg tcacaagcgt tgtccggaat tactgggtgt    540
aaagggagcg caggcgggga gacaagttgg aagtgaaatc tatgggctca acccataaac    600
tgctttcaaa actgttttc ttgagtagtg cagaggtagg cggaattccc ggtgtagcgg    660
tggaatgcgt agatatcggg aggaacacca gtggcgaagg cggcctactg gcaccaact    720 gacgctgagg ctcgaaagtg tgggtagcaa acaggattag ataccctggt agtccacacc    780
gtaaacgatg attactaggt gttggaggat tgacccctc agtgccgcag ttaacacaat    840
aagtaatcca cctggggagt acgaccgcaa ggttgaaact caaaggaatt gacggggggc    900
cgcacaagca gtggagtatg tggtttaatt cgacgcaacg cgaagaacct taccaagtct    960
tgacatccct tgacagacat agaaatatgt attctcttcg gagcaaggag acaggtggtg    1020
catggttgtc gtcagctcgt gtcgtgagat gttgggttaa gtcccgcaac gagcgcaacc    1080
cttatggtca gttactacgc aagaggactc tggccagact gccgttgaca aaacggagga    1140
aggtggggat gacgtcaaat catcatgccc tttatgactt gggctacaca cgtactacaa    1200
tggcgttaaa caaagagaag caagaccgcg aggtgggagca aaactcagaa acaacgtccc    1260
```

| | |
|---|---:|
| agttcggact gcaggctgca actcgcctgc acgaagtcgg aattgctagt aatcgtggat | 1320 |
| cagcatgcca cggtgaatac gttcccgggc cttgtacaca ccgcccgtca caccatgaga | 1380 |
| gccgggggga cccgaagtcg gtagtctaac cgcaaggagg acgccgccga aggtaaaact | 1440 |
| ggtgattggg gtgaagtcgt aacaaggtag ccgt | 1474 |

<210> SEQ ID NO 2
<211> LENGTH: 1474
<212> TYPE: DNA
<213> ORGANISM: Faecalibacterium prausnitzii

<400> SEQUENCE: 2

| | |
|---|---:|
| agagtttgat cctggctcag gacgaacgct ggcggcgcgc ctaacacatg caagtcgaac | 60 |
| gagcgagaga gagcttgctt tctcgagcga gtggcgaacg ggtgagtaac gcgtgaggaa | 120 |
| cctgcctcaa agagggggac aacagttgga aacgactgct aataccgcat aagcccacgg | 180 |
| gtcggcatcg accagaggga aaaggagcaa tccgctttga gatggcctcg cgtccgatta | 240 |
| gctagttggt gaggtaatgg cccaccaagg caacgatcgg tagccggact gagaggttga | 300 |
| acggccacat tgggactgag acgcggccca gactcctacg ggaggcagca gtggggaata | 360 |
| ttgcacaatg ggggaaaccc tgatgcagcg acgccgcgtg gaggaagaag gtcttcggat | 420 |
| tgtaaactcc tgttgttggg gaagataatg acggtaccca acaaggaagt gacggctaac | 480 |
| tacgtgccag cagccgcggt aaaacgtagg tcacaagcgt tgtccggaat tactgggtgt | 540 |
| aaagggagcg caggcgggaa gacaagttgg aagtgaaatc tatgggctca acccataaac | 600 |
| tgctttcaaa actgttttc ttgagtagtg cagaggtagg cggaattccc ggtgtagcgg | 660 |
| tggaatgcgt agatatcggg aggaacacca gtggcgaagg cggcctactg gcaccaact | 720 |
| gacgctgagg ctcgaaagtg tgggtagcaa acaggattag ataccctggt agtccacacc | 780 |
| gtaaacgatg gttactaggt gttggaggat tgaccccttc agtgccgcag ttaacacaat | 840 |
| aagtaatcca cctggggagt acgaccgcaa ggttgaaact caaaggaatt gacggggggcc | 900 |
| cgcacaagca gtggagtatg tggtttaatt cgacgcaacg cgaagaacct taccaagtct | 960 |
| tgacatccct tgacagacat agaaatatgt aatctcttcg gagcaaggag acaggtggtg | 1020 |
| catggttgtc gtcagctcgt gtcgtgagat gttgggttaa gtcccgcaac gagcgcaacc | 1080 |
| cttatggtca gttactacgc aagaggactc tggccagact gccgttgaca aaacggagga | 1140 |
| aggtggggat gacgtcaaat catcatgccc tttatgactt gggctacaca cgtactacaa | 1200 |
| tggcgttaaa caaagagaag caagaccgcg aggtggagca aaactcagaa acaacgtccc | 1260 |
| agttcggact gcaggctgca actcgcctgc acgaagtcgg aattgctagt aatcgtggat | 1320 |
| cagcatgcca cggtgaatac gttcccgggc cttgtacaca ccgcccgtca caccatgaga | 1380 |
| gccgggggga cccgaagtcg gtagtctaac cgcaaggagg acgccgccga aggtaaaact | 1440 |
| ggtgattggg gtgaagtcgt aacaaggtag ccgt | 1474 |

<210> SEQ ID NO 3
<211> LENGTH: 1408
<212> TYPE: DNA
<213> ORGANISM: Faecalibacterium prausnitzii

<400> SEQUENCE: 3

| | |
|---|---:|
| gcgagagaga gcttgctttc tcgagcgagt ggcgaacggg tgagtaacgc gtgaggaacc | 60 |
| tgcctcaaag aggggacaa cagttggaaa cgactgctaa taccgcataa gcccacggcc | 120 |
| cggcatcggg cagagggaaa aggagcaatc cgctttgaga tggcctcgcg tccgattagc | 180 |

| | |
|---|---|
| tagttggtga ggtaacggcc caccaaggcg acgatcggta gccggactga gaggttgaac | 240 |
| ggccacattg ggactgagac acggcccaga ctcctacggg aggcagcagt ggggaatatt | 300 |
| gcacaatggg ggaaaccctg atgcagcgac gccgcgtgga ggaagaaggt cttcggattg | 360 |
| taaactcctg ttgttgagga agataatgac ggtactcaac aaggaagtga cggctaacta | 420 |
| cgtgccagca gccgcggtaa aacgtaggtc acaagcgttg tccggaatta ctgggtgtaa | 480 |
| agggagcgca ggcgggaaga caagttggaa gtgaaatcca tgggctcaac ccatgaactg | 540 |
| ctttcaaaac tgttttctt gagtagtgca gaggtaggcg gaattcccgg tgtagcggtg | 600 |
| gaatgcgtag atatcgggag gaacaccagt ggcgaaggcg gcctactggg caccaactga | 660 |
| cgctgaggct cgaaagtgtg ggtagcaaac aggattagat accctggtag tccacaccgt | 720 |
| aaacgatgat tactaggtgt tggaggattg accccttcag tgccgcagtt aacacaataa | 780 |
| gtaatccacc tggggagtac gaccgcaagg ttgaaactca aaggaattga cgggggcccg | 840 |
| cacaagcagt ggagtatgtg gtttaattcg acgcaacgcg aagaaccta ccaagtcttg | 900 |
| acatcctgcg acggttctgg aaacagaact ttccttcggg acgcagagac aggtggtgca | 960 |
| tggttgtcgt cagctcgtgt cgtgagatgt tgggttaagt cccgcaacga gcgcaaccct | 1020 |
| tatggtcagt tactacgcaa gaggactctg gccagactgc cgttgacaaa acggaggaag | 1080 |
| gtggggatga cgtcaaatca tcatgccctt tatgacttgg gctacacacg tactacaatg | 1140 |
| gcgttaaaca aagagaagca agaccgcgag gtggagcaaa actcagaaac aacgtcccag | 1200 |
| ttcggactgc aggctgcaac tcgcctgcac gaagtcggaa ttgctagtaa tcgtggatca | 1260 |
| gcatgccacg gtgaatacgt tcccgggcct tgtacacacc gcccgtcaca ccatgagagc | 1320 |
| cggggggacc cgaagtcggt agtctaaccg caaggaggac gccgccgaag gtaaaactgg | 1380 |
| tgattggggt gaagtcgtaa caaggtag | 1408 |

<210> SEQ ID NO 4
<211> LENGTH: 1405
<212> TYPE: DNA
<213> ORGANISM: Faecalibacterium prausnitzii

<400> SEQUENCE: 4

| | |
|---|---|
| agcgagagag agcttgcttt ctcgagcgag tggcgaacgg gtgagtaacg cgtgaggaac | 60 |
| ctgcctcaaa gaggggggaca acagttggaa acgactgcta ataccgcata agcccacggt | 120 |
| gccgcatggc acagagggaa aaggagcaat ccgctttgag atggcctcgc gtccgattag | 180 |
| ctagttggtg aggtaacggc ccaccaaggc gacgatcggt agccggactg agaggttgaa | 240 |
| cggccacatt gggactgaga cacggcccag actcctacgg gaggcagcag tggggaatat | 300 |
| tgcacaatgg gggaaaccct gatgcagcga cgccgcgtgg aggaagaagg tcttcggatt | 360 |
| gtaaactcct gttgttgggg aagataatga cggtacccaa caaggaagtg acggctaact | 420 |
| acgtgccagc agccgcggta aaacgtaggt cacaagcgtt gtccggaatt actgggtgta | 480 |
| aagggagcgc aggcgggaag acaagttgga agtgaaatct atgggctcaa cccataaact | 540 |
| gctttcaaaa ctgttttct tgagtagtgc agaggtaggc ggaattcccg gtgtagcggt | 600 |
| ggaatgcgta gatatcggga ggaacaccag tggcgaaggc ggcctactgg gcaccaactg | 660 |
| acgctgaggc tcgaaagtgt gggtagcaaa caggattaga taccctggta gtccacaccg | 720 |
| taaacgatga ttactaggtg ttggaggatt gaccccttca gtgccgcagt taacacaata | 780 |
| agtaatccac ctggggagta cgaccgcaag gttgaaactc aaaggaattg acggggggccc | 840 |

```
gcacaagcag tggagtatgt ggtttaattc gacgcaacgc gaagaacctt accaagtctt      900
gacatccctt gacaggcata gaaatatgtt ttctcttcgg agcaaggaga caggtggtgc      960
atggttgtcg tcagctcgtg tcgtgagatg ttgggttaag tcccgcaacg agcgcaaccc     1020
ttatggtcag ttactacgca agaggactct ggccagactg ccgttgacaa acggaggaa      1080 ggtggggatg acgtcaaatc atcatgccct ttatgacttg gctacacac gtactacaat      1140 ggcgttaaac aaagagaagc aagaccgcga ggtggagcaa aactcagaaa caacgtccca     1200
gttcggactg caggctgcaa ctcgcctgca cgaagtcgga attgctagta atcgtggatc     1260
agcatgccac ggtgaatacg ttcccgggcc ttgtacacac cgcccgtcac accatgagag     1320
ccggggggac ccgaagtcgg tagtctaacc gcaaggagga cgccgccgaa ggtaaaactg     1380
gtgattgggg tgaagtcgta acaag                                           1405

<210> SEQ ID NO 5
<211> LENGTH: 1385
<212> TYPE: DNA
<213> ORGANISM: Faecalibacterium prausnitzii

<400> SEQUENCE: 5
cgagtggcga acgggtgagt aacgcgtgag gaacctgcct caaagagggg gacaacagtt       60
ggaaacgact gctaataccg cataagccca caggtcggca tcgaccagag ggaaaaggag      120
caatccgctt tgagatggcc tcgcgtccga ttagctagtt ggtgaggtaa tggcccacca      180
aggcaacgat cggtagccgg actgagaggt tgaacggcca cattgggact gagacacggc      240
ccagactcct acgggaggca gcagtgggga atattgcaca atgggggaaa ccctgatgca      300
gcgacgccgc gtggaggaag aaggtcttcg gattgtaaac tcctgttgtt gaggaagata      360
atgacggtac tcaacaagga agtgacggct aactacgtgc cagcagccgc ggtaaaacgt      420
aggtcacaag cgttgtccgg aattactggg tgtaaaggga gcgcaggcgg aagacaagt      480 tggaagtgaa atctatgggc tcaacccata aactgctttc aaaactgttt ttcttgagta      540
gtgcagaggt aggcggaatt cccggtgtag cggtggaatg cgtagatatc gggaggaaca      600
ccagtggcga aggcggccta ctgggcacca actgacgctg aggctcgaaa gtgtgggtag      660
caaacaggat tagataccct ggtagtccac accgtaaacg atgattacta ggtgttggag      720
gattgacccc ttcagtgccg cagttaacac aataagtaat ccacctgggg agtacgaccg      780
caaggttgaa actcaaagga attgacgggg cccgcacaa gcagtggagt atgtggttta      840 attgacgca acgcgaagaa ccttaccaag tcttgacatc ctgtgacgat gctgaaaca      900 tgttttttcct tcggaacgca gagacaggtg gtgcatggtt gtcgtcagct cgtgtcgtga      960
gatgttgggt taagtcccgc aacgagcgca acccttactg tcagttacta cgcaagagga     1020
ctctggcagg actgccgttg acaaaacgga ggaaggtggg gatgacgtca atcatcatg     1080 ccctttatga cttgggctac acacgtacta caatggcgtt aaacaaagag aagcaagacc     1140
gcgaggtgga gcaaaactca gaaacaacgt cccagttcgg actgcaggct gcaactcgcc     1200
tgcacgaagt cggaattgct agtaatcgtg gatcagcatg ccacggtgaa tacgttcccg     1260
ggccttgtac acaccgcccg tcacaccatg agagccgggg ggacccgaag tcggtagtct     1320
aaccgcaagg aggacgccgc cgaaggtaaa actggtgatt ggggtgaagt cgtaacaagg     1380
tagcc                                                                 1385

<210> SEQ ID NO 6
<211> LENGTH: 1405
```

```
<212> TYPE: DNA
<213> ORGANISM: Faecalibacterium prausnitzii

<400> SEQUENCE: 6
cgagcgagag agagcttgct ttctcaatcg agtggcgaac gggtgagtaa cgcgtgagga      60
acctgcctca agagggggga caacagttgg aaacgactgc taataccgca taagcccaca     120
ggtcggcatc gaccagaggg aaaaggagca atccgctttg agatggcctc gcgtccgatt     180
agctagttgg tgaggtaatg gcccaccaag gcaacgatcg gtagccggac tgagaggttg     240
aacggccaca ttgggactga cacggccc agactcctac gggaggcagc agtggggaat      300
attgcacaat gggggaaacc ctgatgcagc gacgccgcgt ggaggaagaa ggtcttcgga     360
ttgtaaactc ctgttgttga ggaagataat gacggtactc aacaaggaag tgacggctaa     420
ctacgtgcca gcagccgcgg taaaacgtag gtcacaagcg ttgtccggaa ttactgggtg     480
taaagggagc gcaggcggga agacaagttg gaagtgaaat ctatgggctc aacccataaa     540
ctgctttcaa aactgttttt cttgagtagt gcagaggtag gcggaattcc cggtgtagcg     600
gtggaatgcg tagatatcgg aggaacacc agtggcgaag gcggcctact gggcaccaac     660
tgacgctgag gctcgaaagt gtgggtagca aacaggatta atacc ctgg tagtccacac     720
cgtaaacgat gattactagg tgttggagga ttgaccccctt cagtgccgca gttaacacaa     780
taagtaatcc acctggggag tacgaccgca aggttgaaac tcaaaggaat tgacggggggc     840
ccgcacaagc agtggagtat gtggtttaat tcgacgcaac gcgaagaacc ttaccaagtc     900
ttgacatcct gtgacgaacc tggaaatatg ttttccttc ggaacgcaga gacaggtggt     960
gcatggttgt cgtcagctcg tgtcgtgaga tgttgggtta agtcccgcaa cgagcgcaac    1020
ccttactgtc agttactacg caagaggact ctggcaggac tgccgttgac aaaacggagg    1080
aaggtgggga tgacgtcaaa tcatcatgcc ctttatgact tgggctacac acgtactaca    1140
atggcgttaa acaaagagaa gcaagaccgc gaggtggagc aaaactcaga acaacgtcc    1200
cagttcggac tgcaggctgc aactcgcctg cacgaagtcg gaattgctag taatcgtgga    1260
tcagcatgcc acggtgaata cgttcccggg ccttgtacac accgcccgtc acaccatgag    1320
agccgggggg acccgaagtc ggtagtctaa ccgcaaggag gacgccgccg aaggtaaaac    1380
tggtgattgg ggtgaagtcg tacag                                         1405

<210> SEQ ID NO 7
<211> LENGTH: 1474
<212> TYPE: DNA
<213> ORGANISM: Faecalibacterium prausnitzii

<400> SEQUENCE: 7
agagtttgat cctggctcag gacgaacgct ggcggcgcgc ctaacacatg caagtcgaac      60
gagcgagaga gagcttgctt tctcgagcga gtggcgaacg ggtgagtaac gcgtggggaa     120
cctgcctcaa agagggggac aacagttgga aacgactgct aataccgcat aagcccacga     180
cctggcatcg ggttgaggga aaaggagcaa tccgctttga gatggcctcg cgtccgatta     240
gctagttggt gaggtaatgg cccaccaagg caacgatcgg tagccggact gagaggttga     300
acggccacat tgggactgag acacggccca gactcctacg ggaggcagca gtggggaata     360
ttgcacaatg ggggaaaccc tgatgcagcg acgccgcgtg gaggaagaag gtcttcggat     420
tgtaaactcc tgttgttgag gaagataatg acgtactca acaaggaagt gacggctaac     480
tacgtgccag cagccgcggt aaaacgtagg tcacaagcgt tgtccggaat tactgggtgt     540
```

| | |
|---|---|
| aaagggagcg caggcgggaa gacaagttgg aagtgaaatc catgggctca acccatgaac | 600 |
| tgctttcaaa actgttttc ttgagtagtg cagaggtagg cggaattccc ggtgtagcgg | 660 |
| tggaatgcgt agatatcggg aggaacacca gtggcgaagg cggcctactg gcaccaact | 720 |
| gacgctgagg ctcgaaagtg tgggtagcaa acaggattag ataccctggt agtccacacc | 780 |
| gtaaacgatg attactaggt gttggaggat tgaccccttc agtgccgcag ttaacacaat | 840 |
| aagtaatcca cctggggagt acgaccgcaa ggttgaaact caaaggaatt gacggggggcc | 900 |
| cgcacaagca gtggagtatg tggtttaatt cgacgcaacg cgaagaaccct taccaagtct | 960 |
| tgacatcctg cgacggtgct ggaaacagtg ctttccttcg ggacgcagag acaggtggtg | 1020 |
| catggttgtc gtcagctcgt gtcgtgagat gttgggttaa gtcccgcaac gagcgcaacc | 1080 |
| cttatggtca gttactacgc aagaggactc tggccagact gccgttgaca aaacggagga | 1140 |
| aggtggggat gacgtcaaat catcatgccc tttatgactt gggctacaca cgtactacaa | 1200 |
| tggcgttaaa caaagagaag caagaccgcg aggtggagca aaactcagaa caacgtccc | 1260 |
| agttcggact gcaggctgca actcgcctgc acgaagtcgg aattgctagt aatcgtggat | 1320 |
| cagcatgcca cggtgaatac gttcccgggc cttgtacaca ccgcccgtca caccatgaga | 1380 |
| gccgggggga cccgaagtcg gtagtctaac cgcaaggagg acgccgccga aggtaaaact | 1440 |
| ggtgattggg gtgaagtcgt aacaaggtag ccgt | 1474 |

<210> SEQ ID NO 8
<211> LENGTH: 1533
<212> TYPE: DNA
<213> ORGANISM: Faecalibacterium prausnitzii

<400> SEQUENCE: 8

| | |
|---|---|
| gcatgctcga gcggccgcca gtgtgatgga tatctgcaga attcgccctt agagtttgat | 60 |
| cctggctcag gacgaacgct ggcggcgcgc ctaacacatg caagtcgaac gagcgagaga | 120 |
| gagcttgctt tctcgagcga gtggcgaacg ggtgagtaac gcgtgaggaa cctgcctcaa | 180 |
| agaggggggac aacagttgga aacgactgct aataccgcat aagcccacga cccggcatcg | 240 |
| ggtagaggga aaaggagcaa tccgctttga gatggcctcg cgtccgatta gctagttggt | 300 |
| gaggtaacgg cccaccaagg cgacgatcgg tagccggact gagaggttga acggccacat | 360 |
| tgggactgag acacggccca gactcctacg ggaggcagca gtggggaata ttgcacaatg | 420 |
| ggggaaaccc tgatgcagcg acgccgcgtg aggaagaag gtcttcggat tgtaaactcc | 480 |
| tgttgttgag gaagataatg acggtactca acaggaagt gacggctaac tacgtgccag | 540 |
| cagccgcggt aaacgtagg tcacaagcgt tgtccggaat tactgggtgt aaagggagcg | 600 |
| caggcgggaa gacaagttgg aagtgaaatc catgggctca acccatgaac tgctttcaaa | 660 |
| actgtttttc ttgagtagtg cagaggtagg cggaattccc ggtgtagcgg tggaatgcgt | 720 |
| agatatcggg aggaacacca gtggcgaagg cggcctactg gcaccaact gacgctgagg | 780 |
| ctcgaaagtg tgggtagcaa acaggattag ataccctggt agtccacacc gtaaacgatg | 840 |
| attactaggt gttggaggat tgaccccttc agtgccgcag ttaacacaat aagtaatcca | 900 |
| cctggggagt acgaccgcaa ggttgaaact caaaggaatt gacggggggcc cgcacaagca | 960 |
| gtggagtatg tggtttaatt cgacgcaacg cgaagaaccct taccaagtct tgacatcctg | 1020 |
| cgacggttct ggaaacagaa ctttccttcg ggacgcagag acaggtggtg catggttgtc | 1080 |
| gtcagctcgt gtcgtgagat gttgggttaa gtcccgcaac gagcgcaacc cttatggtca | 1140 |
| gttactacgc aagaggactc tggccagact gccgttgaca aaacggagga aggtggggat | 1200 |

```
gacgtcaaat catcatgccc tttatgactt gggctacaca cgtactacaa tggcgttaaa    1260
caaagagaag caagaccgcg aggtggagca aaactcagaa acaacgtccc agttcggact    1320
gcaggctgca actcgcctgc acgaagtcgg aattgctagt aatcgtggat cagcatgcca    1380
cggtgaatac gttcccgggc cttgtacaca ccgcccgtca ccatgagag ccgggggga     1440 cccgaagtcg gtagtctaac cgcaaggagg acgccgccga aggtaaaact ggtgattggg    1500
gtgaagtcgt aacaaggtag ccgtaagggc gaa                                 1533

<210> SEQ ID NO 9
<211> LENGTH: 1286
<212> TYPE: DNA
<213> ORGANISM: Faecalibacterium prausnitzii

<400> SEQUENCE: 9
gcatcgggca gagggaaaag gagcaatccg ctttgagatg gcctcgcgtc cgattagcta     60
gttggtgagg taatggccca ccaaggcgac gatcggtagc cggactgaga ggttgaacgg    120
ccacattggg actgagacac ggcccagact cctacgggag gcagcagtgg ggaatattgc    180
acaatggggg aaaccctgat gcagcgacgc cgcgtggagg aagaaggtct tcggattgta    240
aactcctgtt gttgaggaag ataatgacgg tactcaacaa ggaagtgacg ctaactacg     300 tgccagcagc cgcggtaaaa cgtaggtcac aagcgttgtc cggaattact gggtgtaaag    360
ggagcgcagg cgggaagaca gttggaagt gaaatccatg gctcaaccc atgaactgct     420 ttcaaaactg ttttcttga gtagtgcaga ggtaggcgga attcccggtg tagcggtgga    480
atgcgtagat atcgggagga acaccagtgg cgaaggcggc ctactgggca ccaactgacg    540
ctgaggctcg aaagtgtggg tagcaaacag gattagatac cctggtagtc cacactgtaa    600
acgatgatta ctaggtgttg gaggattgac cccttcagtg ccgcagttaa cacaataagt    660
aatccacctg gggagtacga ccgcaaggtt gaaactcaaa ggaattgacg ggggcccgca    720
caagcagtgg agtatgtggt ttaattcgac gcaacgcgaa gaaccttacc aagtcttgac    780
atcctgcgac gcacatagaa atatgtgttt ccttcgggac gcagagacag gtggtgcatg    840
gttgtcgtca gctcgtgtcg tgagatgttg ggttaagtcc cgcaacgagc gcaacccta    900 tggtcagtta ctacgcaaga ggactctggc cagactgccg ttgacaaaac ggaggaaggt    960
ggggatgacg tcaaatcatc atgccctta tgacttgggc tacacacgta ctacaatggc    1020
gttaaacaaa gagaagcaag accgcgaggt ggagcaaaac tcagaaacaa cgtcccagtt    1080
cggactgcag gctgcaactc gcctgcacga agtcggaatt gctagtaatc gcagatcagc    1140
atgctgcggt gaatacgttc ccgggccttg tacaccgcc cgtcacacc atgagagccg    1200 gggggacccg aagtcggtag tctaaccgca aggaggacgc cgccgaaggt aaaactggtg    1260
attggggtga agtcgtaaca aggtag                                         1286

<210> SEQ ID NO 10
<211> LENGTH: 1407
<212> TYPE: DNA
<213> ORGANISM: Faecalibacterium prausnitzii

<400> SEQUENCE: 10
cgagcgagag agagcttgct ttctcgagcg agtggcgaac gggtgagtaa cgcgtgagga     60
acctgcctca agaggggga caacagttgg aaacgactgc taataccgca taagcccacg    120
ggtcggcatc gaccagaggg aaaaggagca atccgctttg agatggcctc gcgtccgatt    180
```

```
agctagttgg tgaggtaacg gcccaccaag gcaacgatcg gtagccggac tgagaggttg    240
aacggccaca ttgggactga gacacggccc agactcctac gggaggcagc agtggggaat    300
attgcacaat gggggaaacc ctgatgcagc gacgccgcgt ggaggaagaa ggtcttcgga    360
ttgtaaactc ctgttgttgg ggaagataat gacggtaccc aacaaggaag tgacggctaa    420
ctacgtgcca gcagccgcgg taaaacgtag gtcacaagcg ttgtccggaa ttactgggtg    480
taaagggagc gcaggcggga agacaagttg gaagtgaaat ctatgggctc aacccataaa    540
ctgctttcaa aactgttttt cttgagtagt gcagaggtag gcggaattcc cggtgtagcg    600
gtggaatgcg tagatatcgg gaggaacacc agtggcgaag gcggcctact gggcaccaac    660
tgacgctgag gctcgaaagt gtgggtagca acaggatta gatacctgg tagtccacac    720 cgtaaacgat gattactagg tgttggagga ttgaccccctt cagtgccgca gttaacacaa    780
taagtaatcc acctggggag tacgaccgca aggttgaaac tcaaaggaat tgacggggc    840 ccgcacaagc agtggagtat gtggtttaat tcgacgcaac gcgaagaacc ttaccaagtc    900
ttgacatccc ttgacagaca tagaaatatg taatctcttc ggagcaagga gacaggtggt    960
gcatggttgt cgtcagctcg tgtcgtgaga tgttgggtta agtcccgcaa cgagcgcaac    1020
ccttatggtc agttactacg caagaggact ctggccagac tgccgttgac aaaacggagg    1080
aaggtgggga tgacgtcaaa tcatcatgcc ctttatgact tgggctacac acgtactaca    1140
atggcgttaa acaaagagaa gcaagaccgc gaggtggagc aaaactcaga acaacgtcc    1200 cagttcggac tgcaggctgc aactcgcctg cacgaagtcg gaattgctag taatcgtgga    1260
tcagcatgcc acggtgaata cgttcccggg ccttgtacac accgcccgtc acaccatgag    1320
agccgggggg acccgaagtc ggtagtctaa ccgcaaggag gacgccgccg aaggtaaaac    1380
tggtgattgg ggtgaagtcg taacaag                                        1407
```

<210> SEQ ID NO 11
<211> LENGTH: 1382
<212> TYPE: DNA
<213> ORGANISM: Faecalibacterium prausnitzii

<400> SEQUENCE: 11

```
gagcgagtgg cgaacgggtg agtaacgcgt gaggaacctg cctcaaagag ggggacaaca     60
gttggaaacg actgctaata ccgcataagc ccacgacccg gcatcgggta gagggaaaag    120
gagcaatccg ctttgagatg gcctcgcgtc cgattagcta gttggtgagg taatggccca    180
ccaaggcgac gatcggtagc cggactgaga ggttgaacgg ccacattggg actgagacac    240
ggcccagact cctacgggag gcagcagtgg ggaatattgc acaatggggg aaaccctgat    300
gcagcgacgc cgcgtggagg aagaaggtct tcggattgta aactcctgtt gttgaggaag    360
ataatgacgg tactcaacaa ggaagtgacg gctaactacg tgccagcagc cgcggtaaaa    420
cgtaggtcac aagcgttgtc cggaattact gggtgtaaag ggagcgcagg cgggaagaca    480
agttggaagt gaaatccatg gctcaaccc atgaactgct tcaaaactg tttttcttga    540 gtagtgcaga ggtaggcgga attcccggtg tagcggtgga atgcgtagat atcgggagga    600
acaccagtgg cgaaggcggc ctactgggca ccaactgacg ctgaggctcg aaagtgtggg    660
tagcaaacag gattagatac cctggtagtc cacactgtaa acgatgatta ctaggtgttg    720
gaggattgac cccttcagtg ccgcagttaa cacaataagt aatccacctg gggagtacga    780
ccgcaaggtt gaaactcaaa ggaattgacg ggggcccgca caagcagtgg agtatgtggt    840
ttaattcgac gcaacgcgaa gaaccttacc aagtcttgac atcctgcgac gcacatagaa    900
```

```
atatgtgttt ccttcgggac gcagagacag gtggtgcatg gttgtcgtca gctcgtgtcg    960
tgagatgttg ggttaagtcc cgcaacgagc gcaacccttta tggtcagtta ctacgcaaga   1020
ggactctggc cagactgccg ttgacaaaac ggaggaaggt ggggatgacg tcaaatcatc   1080 atgccctta tgacttgggc tacacacgta ctacaatggc gttaaacaaa gagaagcaag    1140
accgcgaggt ggagcaaaac tcagaaacaa cgtcccagtt cggactgcag gctgcaactc   1200
gcctgcacga agtcggaatt gctagtaatc gcagatcagc atgctgcggt gaatacgttc   1260
ccgggccttg tacacaccgc ccgtcacacc atgagagccg gggggacccg aagtcggtag   1320
tctaaccgca aggaggacgc cgccgaaggt aaaactggtg attggggtga agtcgtaaca   1380
ag                                                                  1382

<210> SEQ ID NO 12
<211> LENGTH: 1395
<212> TYPE: DNA
<213> ORGANISM: Faecalibacterium prausnitzii

<400> SEQUENCE: 12
agcttgcttt ctcgagcgag tggcgaacgg gtgagtaacg cgtgaggaac ctgcctcaaa     60 gaggggaca acagttggaa cgactgcta ataccgcata agcccacggg tcggcatcga     120
ccagagggaa aaggagcaat ccgctttgag atggcctcgc gtccgattag ctagttggtg    180
aggtaacggc ccaccaaggc gacgatcggt agccggactg agaggttgaa cggccacatt    240
gggactgaga cacggcccag actcctacgg gaggcagcag tggggaatat tgcacaatgg    300
gggaaaccct gatgcagcga cgccgcgtgg aggaagaagg tcttcggatt gtaaactcct    360
gttgttgggg aagataatga cggtacccaa caaggaagtg acggctaact acgtgccagc    420
agccgcggta aaacgtaggt cacaagcgtt gtccggaatt actgggtgta aagggagcgc    480
aggcgggaag acaagttgga agtgaaatct atgggctcaa cccataaaact gctttcaaaa    540 ctgttttct tgagtagtgc agaggtaggc ggaattcccg gtgtagcggt ggaatgcgta     600
gatatcggga ggaacaccag tggcgaaggc ggcctactgg gcaccaactg acgctgaggc    660
tcgaaagtgt gggtagcaaa caggattaga taccctggta gtccacaccg taaacgatga    720
ttactaggtg ttggaggatt gaccccttca gtgccgcagt taacacaata agtaatccac    780
ctggggagta cgaccgcaag gttgaaactc aaaggaattg acgggggccc gcacaagcag    840
tggagtatgt ggtttaattc gacgcaacgc gaagaacctt accaagtctt gacatccctt    900
gacagacata gaaatatgta ttctcttcgg agcaaggaga caggtggtgc atggttgtcg    960
tcagctcgtg tcgtgagatg ttgggttaag tcccgcaacg agcgcaaccc ttatggtcag   1020
ttactacgca agaggactct ggccagactg ccgttgacaa acggaggaa ggtgggatg     1080 acgtcaaatc atcatgccct ttatgacttg gctacacac gtactacaat ggcgttaaac   1140
aaagagaagc aagaccgcga ggtggagcaa aactcagaaa caacgtccca gttcggactg    1200
caggctgcaa ctcgcctgca cgaagtcgga attgctagta atcgtggatc agcatgccac   1260
ggtgaatacg ttcccgggcc ttgtacacac cgcccgtcac accatgagag ccggggggac   1320
ccgaagtcgg tagtctaacc gcaaggagga cgccgccgaa ggtaaaactg gtgattgggg   1380
tgaagtcgta acaag                                                    1395

<210> SEQ ID NO 13
<211> LENGTH: 1390
<212> TYPE: DNA
```

<213> ORGANISM: Faecalibacterium prausnitzii

<400> SEQUENCE: 13

| | | | | | |
|---|---|---|---|---|---|
| atcgagtggc | gaacgggtga | gtaacgcgtg | aggaacctgc | ctcaaagagg | gggacaacag | 60 |
| ttggaaacga | ctgctaatac | cgcataagcc | cacggctcgg | catcgagcag | agggaaaagg | 120 |
| agcaatccgc | tttgagatgg | cctcgcgtcc | gattagctag | ttggtgaggt | aatggcccac | 180 |
| caaggcgacg | atcggtagcc | ggactgagag | gttgaacggc | cacattggga | ctgagacacg | 240 |
| gcccagactc | ctacgggagg | cagcagtggg | gaatattgca | caatggggga | aaccctgatg | 300 |
| cagcgacgcc | gcgtggagga | agaaggtctt | cggattgtaa | actcctgttg | ttgaggaaga | 360 |
| taatgacggt | actcaacaag | gaagtgacgg | ctaactacgt | gccagcagcc | gcggtaaaac | 420 |
| gtaggtcaca | agcgttgtcc | ggaattactg | ggtgtaaagg | gagcgcaggc | gggcgatcaa | 480 |
| gttggaagtg | aaatccatgg | gctcaaccca | tgaactgctt | tcaaaactga | ttgtcttgag | 540 |
| tagtgcagag | gtaggcggaa | ttcccggtgt | agcggtggaa | tgcgtagata | tcggaggaa | 600 |
| caccagtggc | gaaggcggcc | tactgggcac | caactgacgc | tgaggctcga | aagtgtgggt | 660 |
| agcaaacagg | attagatacc | ctggtagtcc | acaccgtaaa | cgatgattac | taggtgttgg | 720 |
| aggattgacc | ccttcagtgc | cgcagttaac | acaataagta | atccacctgg | ggagtacgac | 780 |
| cgcaaggttg | aaactcaaag | gaattgacgg | gggcccgcac | aagcagtgga | gtatgtggtt | 840 |
| taattcgacg | caacgcgaag | aaccttacca | agtcttgaca | tcctgcgacg | atgctagaaa | 900 |
| tagtattttc | cttcgggacg | cagagacagg | tggtgcatgg | ttgtcgtcag | ctcgtgtcgt | 960 |
| gagatgttgg | gttaagtccc | gcaacgagcg | caacccttat | ggtcagttac | tacgcaagag | 1020 |
| gactctggcc | agactgccgt | tgacaaaacg | gaggaaggtg | gggatgacgt | caaatcatca | 1080 |
| tgcccttat | gacttgggct | acacacgtac | tacaatggcg | ttaaacaaag | agaagcaaga | 1140 |
| ccgcgaggtg | gagcaaaact | cagaaacaac | gtcccagttc | ggactgcagg | ctgcaactcg | 1200 |
| cctgcacgaa | gtcggaattg | ctagtaatcg | cagatcagca | tgctgcggtg | aatacgttcc | 1260 |
| cgggccttgt | acacaccgcc | cgtcacacca | tgagagccgg | ggggacccga | agtcggtagt | 1320 |
| ctaaccgcaa | ggaggacgcc | gccgaaggta | aaactggtga | ttggggtgaa | gtcgtaacaa | 1380 |
| ggtagccgtc | | | | | | 1390 |

<210> SEQ ID NO 14
<211> LENGTH: 1400
<212> TYPE: DNA
<213> ORGANISM: Faecalibacterium prausnitzii

<400> SEQUENCE: 14

| | | | | | |
|---|---|---|---|---|---|
| gagagagctt | gctttctcaa | gcgagtggcg | aacgggtgag | taacgcgtga | ggaacctgcc | 60 |
| tcaaagaggg | ggacaacagt | tggaaacgac | tgctaatacc | gcataagccc | acgacccggc | 120 |
| atcgggtaga | gggaaaagga | gcaatccgct | ttgagatggc | ctcgcgtccg | attagctagt | 180 |
| tggtgaggta | acggcccacc | aaggcgacga | tcggtagccg | gactgagagg | ttgaacggcc | 240 |
| acattgggac | tgagacacgg | cccagactcc | tacgggaggc | agcagtgggg | aatattgcac | 300 |
| aatgggggaa | accctgatgc | agcgacgccg | cgtggaggaa | gaaggtcttc | ggattgtaaa | 360 |
| ctcctgttgt | tgaggaagat | aatgacggta | ctcaacaagg | aagtgacggc | taactacgtg | 420 |
| ccagcagccg | cggtaaaacg | taggtcacaa | gcgttgtccg | gaattactgg | gtgtaaaggg | 480 |
| agcgcaggcg | gaagacaag | ttggaagtga | atccatggg | ctcaacccat | gaactgcttt | 540 |
| caaaactgtt | tttcttgagt | agtgcagagg | taggcggaat | tcccggtgta | gcggtggaat | 600 |

-continued

```
gcgtagatat cgggaggaac accagtggcg aaggcggcct actgggcacc aactgacgct      660
gaggctcgaa agtgtgggta gcaaacagga ttagataccc tggtagtcca cactgtaaac      720
gatgattact aggtgttgga ggattgaccc cttcagtgcc gcagttaaca caataagtaa      780
tccacctggg gagtacgacc gcaaggttga aactcaaagg aattgacggg gcccgcaca       840 agcagtggag tatgtggttt aattcgacgc aacgcgaaga accttaccaa gtcttgacat      900
cctgcgacgg tgctggaaac agtgcttttcc ttcgggacgc agagacaggt ggtgcatggt     960
tgtcgtcagc tcgtgtcgtg agatgttggg ttaagtcccg caacgagcgc aacccttatg    1020
gtcagttact acgcaagagg actctggcca gactgccgtt gacaaaacgg aggaaggtgg    1080
ggatgacgtc aaatcatcat gccctttatg acttgggcta cacacgtact acaatggcgt    1140
taaacaaaga gaagcaagac cgcgaggtgg agcaaaactc agaaacaacg tcccagttcg    1200
gactgcaggc tgcaactcgc ctgcacgaag tcggaattgc tagtaatcgc agatcagcat    1260
gctgcggtga atacgttccc gggccttgta cacaccgccc gtcacaccat gagagccggg    1320
gggacccgaa gtcggtagtc taaccgcaag gaggacgccg ccgaaggtaa aactggtgat    1380
tggggtgaag tcgtaacaag                                                 1400
```

<210> SEQ ID NO 15
<211> LENGTH: 1388
<212> TYPE: DNA
<213> ORGANISM: Faecalibacterium prausnitzii

<400> SEQUENCE: 15

```
caagcgagtg gcgaacgggt gagtaacgcg tgaggaacct gcctcaaaga gggggacaac       60
agttggaaac gactgctaat accgcataag cccacgaccc ggcatcgggt agagggaaaa      120
ggagcaatcc gctttgagat ggcctcgcgt ccgattagct agttggtgag gtaacggccc      180
accaaggcga cgatcggtag ccggactgag aggttgaacg gccacattgg gactgagaca      240
cggcccagac tcctacggga ggcagcagtg gggaatattg cacaatgggg gaaaccctga      300
tgcagcgacg ccgcgtggag gaagaaggtc ttcggattgt aaactcctgt tgttgaggaa      360
gataatgacg gtactcaaca aggaagtgac ggctaactac gtgccagcag ccgcggtaaa      420
acgtaggtca aagcgttgt ccggaattac tgggtgtaaa gggagcgcag gcggaagac       480 aagttggaag tgaaatccat gggctcaacc catgaactgc tttcaaaact gttttcttg      540 agtagtgcag aggtaggcgg aattcccggt gtagcggtgg aatgcgtaga tatcgggagg      600
aacaccagtg gcgaaggcgg cctactgggc accaactgac gctgaggctc gaaagtgtgg      660
gtagcaaaca ggattagata ccctggtagt ccacactgta aacgatgatt actaggtgtt     720
ggaggattga ccccttcagt gccgcagtta acacaataag taatccacct ggggagtacg     780
accgcaaggt tgaaactcaa aggaattgac ggggcccgc acaagcagtg gagtatgtgg       840
tttaattcga cgcaacgcga gaaccttac caagtcttga catcctgcga cgcacataga      900
aatatgtgtt ccttcggga cgcagagaca ggtggtgcat ggttgtcgtc agctcgtgtc      960
gtgagatgtt gggttaagtc ccgcaacgag cgcaaccctt atggtcagtt actacgcaag    1020
aggactctgg ccagactgcc gttgacaaaa cggaggaagg tggggatgac gtcaaatcat    1080
catgcccttt atgacttggg ctacacacgt actacaatgg cgttaaacaa agagaagcaa    1140
gaccgcgagg tggagcaaaa ctcagaaaca acgtcccagt tcggactgca ggctgcaact    1200
cgcctgcacg aagtcggaat tgctagtaat cgcagatcag catgctgcgg tgaatacgtt    1260
```

| cccgggcctt gtacacaccg cccgtcacac catgagagcc gggggacccc gaagtcggta | 1320 |
| gtctaaccgc aaggaggacg ccgccgaagg taaaactggt gattggggtg aagtcgtaac | 1380 |
| aagggtag | 1388 |

<210> SEQ ID NO 16
<211> LENGTH: 1474
<212> TYPE: DNA
<213> ORGANISM: Faecalibacterium prausnitzii

<400> SEQUENCE: 16

| agagtttgat cctggctcag gacgaacgct ggcggcgcgc ctaacacatg caagtcgaac | 60 |
| gagcgagaga gagcttgctt tctcgagcga gtggcgaacg ggtgagtaac gcgtgaggaa | 120 |
| cctgcctcaa agaggggac aacagttgga aacgactgct aataccgcat aagcccacga | 180 |
| cccggcatcg ggttgaggga aaaggagcaa tccgctttga gatggcctcg cgtccgatta | 240 |
| gctagttggt gaggtaacgg cccaccaagg cgacgatcgg tagccggact gagaggttga | 300 |
| acggccacat tgggactgag acacggccca gactcctacg ggaggcagca gtggggaata | 360 |
| ttgcacaatg ggggaaaccc tgatgcagcg acgccgcgtg aggaagaag gtcttcggat | 420 |
| tgtaaactcc tgttgttggg gaagataatg acggtaccca acaaggaagt gacggctaac | 480 |
| tacgtgccag cagccgcggt aaaacgtagg tcacaagcgt tgtccggaat tactgggtgt | 540 |
| aaagggagcg caggcgggaa gacaagttgg aagtgaaatc catgggctta acccatgaac | 600 |
| tgctttcaaa actgtttttc ttgagtagtg cagaggtagg cggaattccc ggtgtagcgg | 660 |
| tggaatgcgt agatatcggg aggaacacca gtggcgaagg cggcctactg gcaccaact | 720 |
| gacgctgagg ctcgaaagtg tgggtagcaa acaggattag ataccctggt agtccacacc | 780 |
| gtaaacgatg attactaggt gttggaggat gaccccttc agtgccgcag ttaacacaat | 840 |
| aagtaatcca cctggggagt acgaccgcaa ggttgaaact caaaggaatt gacggggcc | 900 |
| cgcacaagca gtggagtatg tggtttaatt cgacgcaacg cgaagaacct taccaagtct | 960 |
| tgacatcctg tgacagacgt agaaatacgt tcttccttcg gacacagag acaggtggtg | 1020 |
| catggttgtc gtcagctcgt gtcgtgagat gttgggttaa gtcccgcaac gagcgcaacc | 1080 |
| cttatggtca gttactacgc aagaggactc tggccagact gccgttgaca aacggagga | 1140 |
| aggtggggat gacgtcaaat catcatgccc tttatgactt gggctacaca cgtactacaa | 1200 |
| tggcgttaaa caaagagaag caagaccgcg aggtggagca aaactcagaa acaacgtccc | 1260 |
| agttcggact gcaggctgca actcgcctgc acgaagtcgg aattgctagt aatcgtggat | 1320 |
| cagcatgcca cggtgaatac gttcccgggc cttgtacaca ccgcccgtca ccatgaga | 1380 |
| gccggggga cccgaagtcg gtagtctaac cgcaaggagg acgccgccga aggtaaaact | 1440 |
| ggtgattggg gtgaagtcgt aacaaggtag ccgt | 1474 |

<210> SEQ ID NO 17
<211> LENGTH: 1323
<212> TYPE: DNA
<213> ORGANISM: Faecalibacterium prausnitzii

<400> SEQUENCE: 17

| ttagtggcga acgggtgagt aacgcgtgag taacctgccc tggagtgggg gacaacagtt | 60 |
| ggaaacgact gctaataccg cataagccca cggcccggca tcgggctgcg ggaaaaggat | 120 |
| ttattcgctt caggatggac tcgcgtccaa ttagctagtt ggtgaggtaa cggcccacca | 180 |
| aggcgacgat tggtagccgg actgagaggt tgaacggcca cattgggact gagacacggc | 240 |

```
ccagactcct acgggaggca gcagtgggggg atattgcaca atgggggaaa ccctgatgca    300
gcgacgccgc gtggaggaag aaggttttcg gattgtaaac tcctgtcgtt agggacgaat    360
catgacggta cctaacaaga aagcaccggc taactacgtg ccagcagccg cggtaaaacg    420
tagggtgcaa gcgttgtccg gaattactgg gtgtaaaggg agcgcaggcg gaccggcaag    480
ttggaagtga aaccatggg ctcaacccat gaattgcttt caaaactgct ggccttgagt    540
agtgcagagg taggtggaat tcccggtgta gcggtggaat gcgtagatat cgggaggaac    600
accagtggcg aaggcgacct actgggcacc aactgacgct gaggctcgaa agcatgggta    660
gcaaacagga ttagataccc tggtagtcca tgccgtaaac gatgattact aggtgttgga    720
ggattgaccc cttcagtgcc gcagttaaca caataagtaa tccacctggg gagtacgacc    780
gcaaggttga aactcaaagg aattgacggg ggcccgcaca agcagtggag tatgtggttt    840
aattcgaagc aacgcgaaga accttaccag gtcttgacat ccgatgcata gtgcagagat    900
gcatgaagtc cttcgggaca tcgagacagg tggtgcatgg ttgtcgtcag ctcgtgtcgt    960
gagatgttgg gttaagtccc gcaacgagcg caacccttat tgccagttac tacgtaagag   1020
gactctggcg agactgccgt tgacaaaacg gaggaaggtg gggatgacgt caaatcatca   1080
tgccctttat gacctgggct acacacgtac tacaatggcg tttaacaaag agaagcaaga   1140
ccgcgaggtg gagcaaaact cagaaacaac gtctcagttc agattgcagg ctgcaactcg   1200
cctgcatgaa gtcggaattg ctagtaatcg cggatcagca tgccgcggtg aatacgttcc   1260
cgggccttgt acacaccgcc cgtcacacca tgagagccgg ggggacccga agtcggtagt   1320
cta                                                                 1323

<210> SEQ ID NO 18
<211> LENGTH: 1469
<212> TYPE: DNA
<213> ORGANISM: Eubacterium desmolans
<220> FEATURE:
<221> NAME/KEY: misc_feature
<222> LOCATION: (31)..(31)
<223> OTHER INFORMATION: n is a, c, g, t or u
<220> FEATURE:
<221> NAME/KEY: misc_feature
<222> LOCATION: (274)..(274)
<223> OTHER INFORMATION: n is a, c, g, t or u
<220> FEATURE:
<221> NAME/KEY: misc_feature
<222> LOCATION: (400)..(400)
<223> OTHER INFORMATION: n is a, c, g, t or u
<220> FEATURE:
<221> NAME/KEY: misc_feature
<222> LOCATION: (574)..(574)
<223> OTHER INFORMATION: n is a, c, g, t or u
<220> FEATURE:
<221> NAME/KEY: misc_feature
<222> LOCATION: (579)..(579)
<223> OTHER INFORMATION: n is a, c, g, t or u
<220> FEATURE:
<221> NAME/KEY: misc_feature
<222> LOCATION: (601)..(601)
<223> OTHER INFORMATION: n is a, c, g, t or u
<220> FEATURE:
<221> NAME/KEY: misc_feature
<222> LOCATION: (916)..(918)
<223> OTHER INFORMATION: n is a, c, g, t or u
<220> FEATURE:
<221> NAME/KEY: misc_feature
<222> LOCATION: (956)..(957)
<223> OTHER INFORMATION: n is a, c, g, t or u
<220> FEATURE:
<221> NAME/KEY: misc_feature
<222> LOCATION: (979)..(979)
```

```
<223> OTHER INFORMATION: n is a, c, g, t or u
<220> FEATURE:
<221> NAME/KEY: misc_feature
<222> LOCATION: (1016)..(1016)
<223> OTHER INFORMATION: n is a, c, g, t or u
<220> FEATURE:
<221> NAME/KEY: misc_feature
<222> LOCATION: (1025)..(1025)
<223> OTHER INFORMATION: n is a, c, g, t or u
<220> FEATURE:
<221> NAME/KEY: misc_feature
<222> LOCATION: (1038)..(1038)
<223> OTHER INFORMATION: n is a, c, g, t or u
<220> FEATURE:
<221> NAME/KEY: misc_feature
<222> LOCATION: (1079)..(1079)
<223> OTHER INFORMATION: n is a, c, g, t or u
<220> FEATURE:
<221> NAME/KEY: misc_feature
<222> LOCATION: (1179)..(1180)
<223> OTHER INFORMATION: n is a, c, g, t or u
<220> FEATURE:
<221> NAME/KEY: misc_feature
<222> LOCATION: (1195)..(1195)
<223> OTHER INFORMATION: n is a, c, g, t or u
<220> FEATURE:
<221> NAME/KEY: misc_feature
<222> LOCATION: (1373)..(1374)
<223> OTHER INFORMATION: n is a, c, g, t or u

<400> SEQUENCE: 18
tttttagaga gtttgatcct ggctcaggat naacgctggc ggcgtgccta acacatgcaa      60
gtcgaacgga gttattttgg aaatctcttc ggagatggaa ttcataactt agtggcggac     120
gggtgagtaa cgcgtgagca atctgccttt aggtggggga taacagtcgg aaacggctgc     180
taataccgca taatacgttt tggggcatcc ttgaaacgtc aaagattta ttgcctttag      240 atgagctcgc gtctgattag ctggttggcg gggnaacggc ccaccaaggc gacgatcagt     300
agccggactg agaggttgaa cggccacatt gggactgaga cacggcccag actcctacgg     360
gaggcagcag tggggaatat tgcgcaatgg gggaaaccen dacgcagcaa cgccgcgtga     420
ttgaagaagg ccttcgggtt gtaaagatct ttaatcaggg acgaattttg acggtacctg     480
aagaataagc tccggctaac tacgtgccag cagccgcggt aatacgtagg gagcaagcgt     540
tatccggatt tactgggtgt aaagggcgcg cagncgggnc ggcaagttgg gagtgaaatc     600
ngggggctta acccccgaac tgctttcaaa actgctggtc ttgagtgatg gagaggcagg     660
cggaattccg tgtgtagcgg tgaaatgcgt agatatacgg aggaacacca gtggcgaagg     720
cggcctgctg gacattaact gacgctgagg cgcgaaagcg tggggagcaa acaggattag     780
ataccctggt agtccacgcc gtaaacgatg gatactaggt gtgggaggta ttgaccccct     840
ccgtgccgca gttaacacaa taagtatccc acctggggag tacggccgca aggttgaaac     900
tcaaaggaat tgacgnnngc ccgcacaagc agtggagtat gtggtttaat tcgaannaac     960
gcgaagaacc ttaccaggnc ttgacatccc ggtgaccgtc ctagagatag gacttnectt    1020 cgggncaacg gtgacagntg gtgcatggtt gtcgtcagct cgtgtcgtga gatgttggnt    1080
taagtcccgc aacgagcgca acccttacgg ttagttgata cgcaagatca ctctagccgg    1140
actgccgttg acaaaacgga ggaaggtggg gacgacgtnn aatcatcatg cccentatga    1200 cctgggctac acacgtacta caatggcagt catacagagg gaagcaaaat cgcgaggtgg    1260
```

-continued

```
agcaaatccc taaaagctgt cccagttcag attgcaggct gcaacccgcc tgcatgaagt    1320
cggaattgct agtaatcgcg gatcagcatg ccgcggtgaa tacgttcccg ggnnttgtac    1380
acaccgcccg tcacaccatg agagccgtca atacccgaag tccgtagcct aaccgcaagg    1440
ggggcgcggc cgaaggtagg ggtggtaat                                      1469
```

FAECALIBACTERIUM PRAUSNITZII STRAINS FOR TREATING AND PREVENTING GASTROINTESTINAL PAIN

FIELD OF THE INVENTION

The present invention concerns *Faecalibacterium prausnitzii* strains for use in the treatment and prevention of visceral abdominal pain in an individual, in particular of gastrointestinal pain of non-inflammatory origin.

The present invention also concerns a composition, in particular an oral composition, comprising specific *Faecalibacterium prausnitzii* strains as well as new *Faecalibacterium prausnitzii* strains per se.

PRIOR ART

Visceral abdominal pain, and in particular gastrointestinal pain, is a very common disorder that affects millions of people every year all over the world and is a leading cause of patient visits to clinics. Abdominal pain is present on questioning of 75 percent of otherwise healthy adolescent students (Hyams et al. J. Pediatr. 1996; 129:220) and in about half of all adults (Heading; Scand J Gastroenterol Suppl. 1999; 231:3).

Such visceral pain can originate from various origins such as peptic disease, pancreatitis in alcoholics, inflammatory bowel disease, appendicitis, ruptured viscus, acute volvulus or even gastritis, biliary colic, gastroenteritis, splenic rupture, hepatic laceration or small bowel rupture.

However, gastrointestinal disorders, in particular non-inflammatory gastrointestinal disorders, and more particularly Irritable Bowel Syndrome (IBS), are the most frequent reasons for visceral abdominal pain in an individual.

IBS is one of the 25 most wide-spread recognized pathologies of the gastrointestinal tract. In the USA and in the first five European countries (France, Germany, the United Kingdom, Spain and Italy), in 2009, IBS affected more than 24 million persons. IBS accounts for 40 to 60% of referrals to gastroenterology outpatient clinics (Jones et al., *Gut* 2000; 47(Suppl 2): ii1-ii19).

Three subgroups of IBS patients have been defined based on the predominant bowel habit: constipation-predominant (c-IBS), diarrhea-predominant (d-IBS) or alternating between 25 the two (a-IBS). The definition and diagnostic criteria for IBS have been formalized in the "Rome Criteria" (Drossman et al. 1999, Gut 45:Suppl II: 1-81).

The pathophysiology of IBS is believed to involve alterations in the brain-gut axis. However, the mechanisms by which these changes lead to IBS remain poorly understood.

IBS is in particular characterized by a colonic hypersensitivity. This pain sensitivity is usually studied using variation of balloon distention in the rectum, a procedure in which a balloon is inserted into the rectum and slowly inflated. This common complaint is a crucial feature because of its significant impact on a patient's quality of life and lack of efficient therapies.

However, the current treatments against IBS and visceral abdominal pain are disappointing.

There is thus a need for new substances, in particular probiotics, or compositions for the treatment and/or prevention of visceral abdominal pain, in particular gastrointestinal pain, in an individual.

There is also a need for new substances, in particular probiotics, or compositions for preventing and/or treating visceral abdominal pain in an individual suffering from a non-inflammatory gastrointestinal disorder, in particular from an Irritable Bowel Syndrome (IBS).

More particularly, there is a need in the prior art for new substances, in particular probiotics, or compositions that are able to diminish the sensitivity of nociceptors in the gastrointestinal tract of an individual, in particular in individuals suffering from a colonic hypersensitivity.

SUMMARY OF THE INVENTION

The present invention aims to provide novel substances, in particular probiotics, and compositions for treating and/or preventing visceral abdominal pain in an individual, more particularly gastrointestinal pain of non-inflammatory origin.

According to the inventors' experimental results, specific *Faecalibacterium prausnitzii* (*F. prausnitzii*) strains, belonging to three particular phylogroups previously described (Lopez-Siles et al., 2012), possess the unexpected ability to diminish visceral abdominal pain in an individual. As illustrated in the Examples and discussed further, the inventors have demonstrated that *F. prausnitzii* strains outside of these phylogroups, such as the strain CNCM I-4541, do not possess such advantageous properties.

The properties of the *F. prausnitzii* strains of the invention have been demonstrated in the examples by the inventor's in two different models: a Neonatal Maternal Separation (NMS) colonic hypersensitivity (CHS) mouse model and a Partial Restraint Stress (PRS) Rat Model.

Strains according to the invention are more particularly able to diminish the sensitivity of nociceptors in the gastrointestinal tract of an individual and consequently to prevent and/or reduce colonic hypersensitivity of said individual.

According to a first object, the present invention relates to a bacterial strain of the *Faecalibacterium prausnitzii* species selected from a bacterial strain belonging to one of the phylogroups I, II and III according to the invention, for use in the treatment and/or prevention of visceral abdominal pain in an individual.

These strains identified by the inventors are thus probiotics that can be used for the above-indicated purposes.

An individual according to the invention is a mammal, in particular a human.

Visceral abdominal pain is pain associated with organs of the abdomen of the individual.

The visceral abdominal pain is in particular a gastrointestinal pain, in particular a colonic pain.

A bacterial strain of the *Faecalibacterium prausnitzii* species according to the invention is different from the strain A2-165.

According to a preferred embodiment, bacterial strains according to the invention for use as indicated here above are selected from the group consisting of bacterial strains deposited to the CNCM under the accession numbers I-4542, I-4544, I-4540, I-4574, I-4543, I-4575, I-4573, I-4644 and I-4546, and in particular the bacterial strain deposited to the CNCM under the accession number I-4573.

According to an embodiment, the visceral pain according to the invention is caused by a gastrointestinal disorder, in particular a non-inflammatory gastrointestinal disorder.

A gastrointestinal disorder of the invention, in particular according to this embodiment, can be a gastrointestinal hypersensitivity, in particular a colonic hypersensitivity, and is preferably an Irritable Bowel Syndrome, in particular an alternating-type Irritable Bowel Syndrome.

In particular, such gastrointestinal disorder according to the invention can be selected from the group consisting of IBS and constipation.

According to another embodiment, a bacterial strain for use according to the invention is comprised in a composition comprising a physiologically acceptable medium, preferably in an oral composition, and most preferably in a food supplement.

Thus, according to another object, the present invention relates to a composition comprising, in a physiologically acceptable medium, at least one bacterial strain of *Faecalibacterium prausnitzii* selected from the group consisting of bacterial strains deposited to the CNCM under the accession numbers I-4542, I-4544, I-4540, I-4574, I-4543, I-4575, I-4573, I-4644 and I-4546.

In a preferred embodiment, said bacterial strain of the *Faecalibacterium prausnitzii* species is the bacterial strain deposited to the CNCM under the accession numbers I-4573.

The term "physiologically acceptable medium" is understood to mean a medium that is compatible with the organism of the individual to whom said composition is intended to be administered. It can for example be any non-toxic solvent such as water. In particular, said medium is compatible with an oral administration.

A composition of the invention is preferably for the oral route and in particular in the form of a food supplement.

A composition of the invention for the oral route can be selected from the group consisting of a food product, a drink, a pharmaceutical, a nutraceutical, a food additive, a food supplement and a dairy product. It can in particular be a food supplement.

The inventors have also indentified new *Faecalibacterium prausnitzii* strains having the specific abilities discussed previously.

Consequently, a further object of the invention consists in an isolated bacterial strain selected from the group consisting of bacterial strains deposited to the CNCM under the accession numbers I-4542, I-4544, I-4540, I-4574, I-4543, I-4575, I-4573, I-4644 and I-4546.

According to a preferred embodiment, said bacterial strain is the bacterial strain deposited to the CNCM under the accession number I-4573.

As demonstrated in the examples, a *Faecalibacterium prausnitzii* strain of the invention has no negative impact in an individual not suffering from visceral abdominal pain according to the invention and is thus perfectly safe for use.

FIGURES' LEGENDS

For illustrative purposes, *Faecalibacterium prausnitzii* strains CNCM I-4541 (SEQ ID No: 16) and S13E3 (SEQ ID No: 17) are outside the three phylogroups of the invention. The method for obtaining said distribution is discussed further below.

Figure 3A:
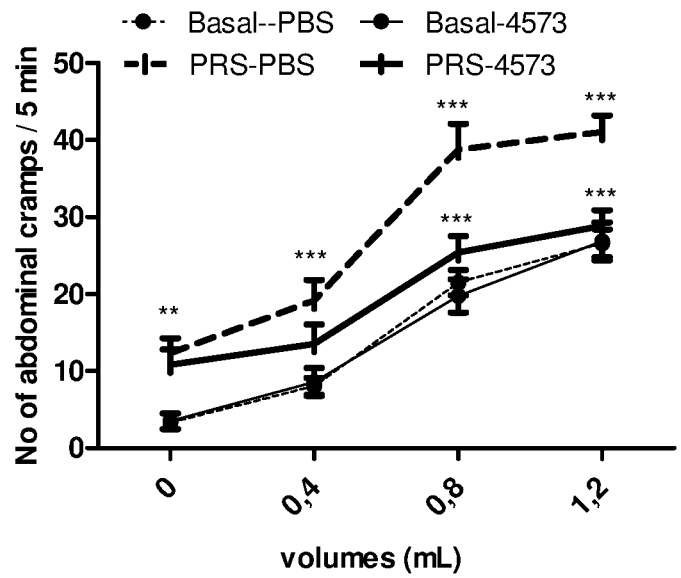

FIG. 3A illustrates the effect of *F. prausnitzii* CNCM I-4573 strain on the number of abdominal cramps/5 minutes in Partial Restraint Stress (PRS) (PRS-4573—continuous slashed line; n=12 rats) or basal rats models (Basal-4573—continuous lines with circles; n=12 rats) compared to PRS or basal rats treated with PBS (respectively PRS-PBS—dotted slashed lines and Basal-PBS—dotted lines with circles; n=18 rats per group), depending on the Distension volume (mL) generated with an arterial embolectomy catheter introduced into the rectum of the rats.

Figure 3B:
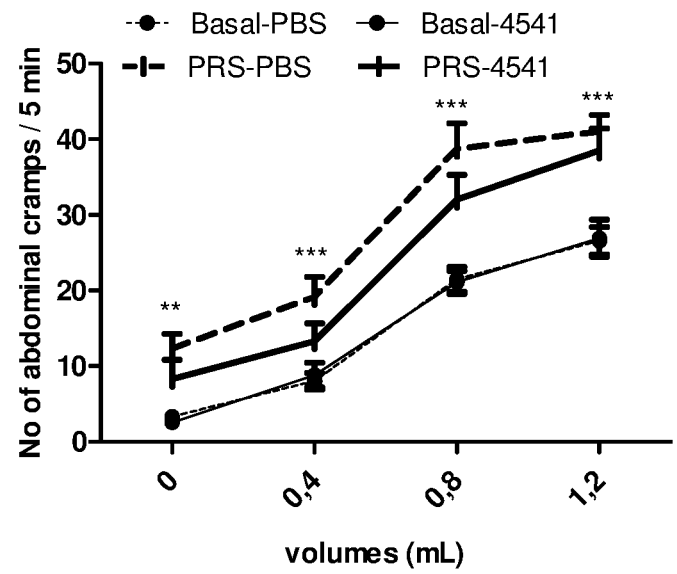

FIG. 3B illustrates the effect of *F. prausnitzii* CNCM I-4541 strain outside of the invention on the number of abdominal cramps/5 minutes in Partial Restraint Stress (PRS) (PRS-4573—continuous slashed line; n=12 rats) or basal rats models (Basal-4573—continuous lines with circles; n=12 rats) compared to PRS or basal rats treated with PBS (respectively PRS-PBS—dotted slashed lines and Basal-PBS—dotted lines with circles; n=18 rats per group), depending on the Distension volume (mL) generated with an arterial embolectomy catheter introduced into the rectum of the rats.

DETAILED DESCRIPTION OF THE INVENTION

The present inventors have performed a huge amount of work with the view of identifying the ability of specific *Faecalibacterium prausnitzii* strains to treat and/or prevent visceral abdominal pain, and in particular gastrointestinal pain, in an individual.

The inventors have indeed unexpectedly determined that *Faecalibacterium prausnitzii* strains belonging to three phylogroups defined further exhibit the ability to diminish the sensitivity of nociceptors in the gastrointestinal tract of an individual.

The bacterial strains according to the invention can prevent and/or reduce visceral abdominal pain, in particular gastrointestinal pain, in an individual, in particular in an individual suffering from a gastrointestinal non-inflammatory disorder, and in particular from a colonic hypersensitivity, such as in IBS.

It is demonstrated herein that bacterial strains of the invention are in particular able to reduce the Vicero Motrice Response (VMR) of a colon when a balloon inserted into the rectum is slowly inflated in an IBS mouse model pre-treated with a bacterial strain of the invention. Said VMR is brought back to a normal intensity, since the VMR level observed after administration of a strain according to the invention is similar to the VMR observed in mice not suffering from colonic hypersensitivity.

*Faecalibacterium prausnitzii* Strains of the Invention

*F. prausnitzii* is a major member of the *Firmicutes phylum* and is part of the most abundant commensal bacteria in the healthy human large intestine microbiota.

*F. prausnitzii* is an extremely oxygen sensitive (EOS) bacterium and is thus difficult to cultivate, even in anaerobic conditions (Duncan et al. 2002, Int. J. Syst. Evol. Microbiol. 52(Pt 6): 2141-6 and Lopez-Siles et al. Appl. Environ Microbiol. 2012 January; 78(2):420-8). *F. prausnitzii* is in particular known as being one of the most abundant butyrate-producing bacterium in the human gastrointestinal tract, the short chain fatty acid butyrate being very important in gut physiology, systemic functions and beneficial effects for human health (Macfarlane and Macfarlane (2011), J. Clin. Gastroenterol. 45 Suppl: S120-7).

*F. prausnitzii* is also known for having anti-inflammatory and protective effects in murine models of acute and chronic colitis, i.e. in inflammatory disorders (Martin et al., Inflamm Bowel Dis. 2014 March; 20(3):417-30 and Sokol et al., Proc Natl Acad Sci USA. 2008 Oct. 28; 105(43):16731-6).

Recently, diminished prevalence and abundance of *F. prausnitzii* have been reported in non-inflammatory intestinal disorders. A negative correlation has indeed been observed between the abundance of *F. prausnitzii* bacteria and IBS symptoms, in particular in alternating-type IBS.

Emerging evidences suggest that perturbation of the gastrointestinal microbiota, and in particular dysbiosis, plays a role in the pathophysiology of IBS (Ringel and Maharshak, Am. J. Physiol. Gastrointest. Liver Physiol. 2013 Oct. 15; 305(8): G529-41).

The ability of the *F. prausnitzii* strains of the invention to prevent visceral abdominal pain, and in particular gastrointestinal pain, in an individual is specific to the strains identified by the inventors, and constituting the three phylogroups of the invention.

Such specific antinociceptive activity is illustrated in the examples, wherein a comparative test has been performed with a *F. prausnitzii* strain not part of the three phylogroups of the invention, i.e. the strain CNCM I-4541. As demonstrated in these examples, this strain does not possess the antinociceptive activity of the strains of the invention.

Method for Obtaining Phylogroups of the Invention

Figure 2:
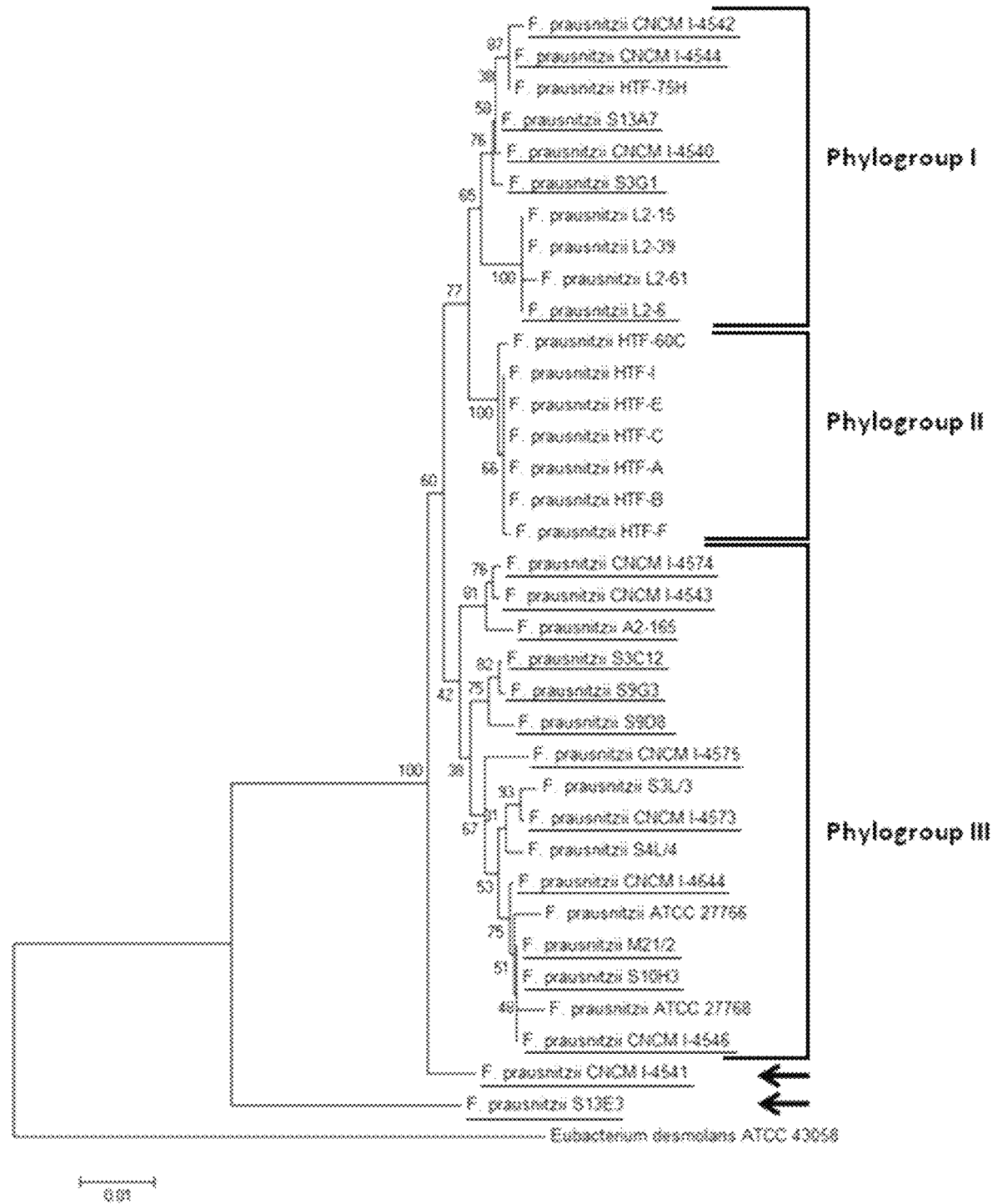
FIG. 2 illustrates 35 *Faecalibacterium prausnitzii* strains and their distribution in or outside of the three phylogroups of the invention.

Isolated *Faecalibacterium prausnitzii* strains have been classified by the inventors in three phylogroups illustrated in FIG. 2 according to 16S rRNA sequences.

Full-length 16S rRNA gene sequences of each strain were obtained or determined and compared one to the other.

Full-length 16S rRNA sequences of 17 *F. prausnitzii* strains are indicated as sequences SEQ ID No: 1 to 17.

DNA was extracted from isolated colonies of the different *F. prausnitzii* strains by alkaline lysis in 50 μL of NaOH 0.5 M during 30 min and 50 μl of Tris 1M pH7 and 100 μL H2O were added.

16S rRNA sequences were amplified and PCR products purified with the Wizard SV Gel. PCR Clean-Up system (Promega) was used to obtain bidirectional partial 16S rRNA gene sequences by using primers. All DNA sequences were confirmed by sequencing (Eurofins MWG Operon, Ebersberg, Germany).

Multiple sequence alignment was performed with hierarchical clustering for 16S rRNA gene sequence full-length construction (http://multalin.toulouse.inra.fr/multalin) (COrpet F., Nucleic Acids Res. 1988; 16:10881-10890).

Phylogenetic analysis of the 16S rRNA gene was then performed using MEGA6 software package (http://www.megasoftware.net/). The evolutionary history was inferred using the Neighbor-Joining method (Saitou N. and Nei M., Mol Biol Evol. 1987; 4:406-425).

The optimal tree with the sum of branch length=0.24930207 is shown in FIG. 2. The percentage of replicate trees in which the associated taxa clustered together in the bootstrap test (500 replicates) are shown next to the branches (Zharkikh A. and Li W H, Mol Phylogenet Evol. 1995; 4:44-63).

The tree is drawn to scale, with branch lengths in the same units as those of the evolutionary distances used to infer the phylogenetic tree. The evolutionary distances were computed using the Maximum Composite Likelihood method (Tamura et al., Proc Natl Acad Sci USA. 2004; 101:11030-11035) and are in the units of the number of base substitutions per site.

The analysis involved 35 nucleotide sequences. Codon positions included were 1st+2nd+3rd+Non-coding. All positions containing gaps and missing data were eliminated.

There were a total of 1091 positions in the final dataset. *Eubacterium desmolans* was used to root the tree (SEQ ID No: 18). In sequence SEQ ID No: 18, 'n' is used to represent any ambiguous nucleotides.

In order to verify if a given *F. prausnitzii* strain can be classified in one of the phylogroups I to III according to the invention, its 16S rRNA sequence needs to be compared through the MEGA6 software package discussed here-above directly to the one of the present invention.

According to an embodiment, a bacterial strain of the invention is selected from phylogroup I.

Bacterial strains belonging to phylogroup I can be represented by the strains consisting of:
  bacterial strains deposited to the CNCM under the accession numbers I-4542, I-4544 and I-4540; and
  bacterial strains of reference HTF-75H, S13A7, S3G1, L2-15, L2-39, L2-61 and L2-6.

Preferably, a bacterial strain belonging to phylogroup I is selected from the group consisting of bacterial strains deposited to the CNCM (Collection Nationale de Cultures de Microorganismes) having an address at 25, Rue du Docteur Roux F-75724 Paris Cedex 15, France under the accession numbers I-4542, I-4544 and I-4540 on Oct. 13, 2011.

According to an embodiment, a bacterial strain of the invention is selected from phylogroup II.

Bacterial strains belonging to phylogroup II can for example be selected from the group consisting of bacterial strains of reference HTF-60C, HTF-I, HTF-E, HTF-C, HTF-A, HTF-B and HTF-F.

According to an embodiment, a bacterial strain of the invention is selected from phylogroup III.

Bacterial strains belonging to phylogroup III can be represented by the strains consisting of:
  bacterial strains deposited to the CNCM under the accession numbers I-4574, I-4543, I-4575, I-4573, I-4644 and I-4546; and
  bacterial strains of reference S3C12, S9G3, S9D8, S3L/3, S4L/4, M21/2 and S10H3,
with the proviso that the bacterial strain is different from the bacterial strain A2-165.

Preferably, a bacterial strain belonging to phylogroup III is selected from the group consisting of bacterial strains deposited to the CNCM (Collection Nationale de Cultures de Microorganismes) having an address at 25, Rue du Docteur Roux F-75724 Paris Cedex 15, France under the accession numbers I-4574, I-4543, I-4575, I-4573, I-4644 and I-4546. Strains I-4573, I-4574 and I-4575 were deposited on Dec. 7, 2011, strains I-4543 and I-4546 were deposited on Oct. 13, 2011, and strain I-4644 was deposited on Jun. 20, 2012.

Bacterial strains of reference ATCC 27768, A2-165, L2-15, L2-39, L2-6, L2-61, M21/2, S3L/3, S4L/4, HTF-A, HTF-B, HTF-C, HTF-E, HTF-F, HTF-I, HTF-60C and HTF-75H can be obtained as indicated in Lopez-Siles et al., Appl. Environ. Microbiol. 2012, 78(2):420.

In a preferred embodiment, a bacterial strain of the invention is selected from phylogroups I and/or III. More particularly, a bacterial strain of the invention is selected from phylogroups I and/or III with the proviso that the bacterial strain is different from the bacterial strain A2-165.

According to an embodiment, a bacterial strain of the invention is selected from the group consisting of bacterial strains deposited to the CNCM under the accession numbers I-4542, I-4544, I-4540, I-4574, I-4543, I-4575, I-4573, I-4644 and I-4546.

A bacterial strain of the invention is preferably the bacterial strain deposited to the CNCM under the accession number I-4573.

The inventors have also indentified new *Faecalibacterium prausnitzii* strains having the specific abilities discussed previously.

Consequently, the present invention further concerns an isolated bacterial strain selected from the group consisting of bacterial strains deposited to the CNCM under the accession numbers I-4542, I-4544, I-4540, I-4574, I-4543, I-4575, I-4573, I-4644 and I-4546.

Said bacterial strain is in particular the bacterial strain deposited to the CNCM under the accession number I-4573.

A suitable daily dose of a bacterial strain according to the invention is from $10^3$ to $10^{12}$ colony forming units (cfu), more preferably from $10^7$ to $10^{11}$ cfu as a medicament, for example as a daily dose equivalent to $10^{10}$ cfu.

A *Faecalibacterium prausnitzii* strain of the invention is for use in the treatment and/or prevention of visceral abdominal pain in an individual.

The strains of the invention are probiotics whose activity lies in the gut. A probiotic bacterium according to the invention denotes a bacterium which ingested live in adequate quantities can exert beneficial effects on the human health.

These strains consequently need to be administered alive to the gut.

The bacteria strains of the invention can be administered to the gut of an individual to be treated by different ways, i.e. by the oral, rectal or parenteral route. A bacterium according to the invention is preferably administered by the oral or rectal route, more preferably by the oral route.

According to a preferred embodiment, a bacterial strain of the invention is comprised in a composition comprising a physiologically acceptable medium. Such composition is preferably for the oral route, and in particular in the form of a food supplement.

Compositions

The present invention further concerns a composition comprising, in a physiologically acceptable medium, at least one bacterial strain of *Faecalibacterium prausnitzii* of the invention.

More particularly, according to an embodiment, the present invention relates to a composition comprising, in a physiologically acceptable medium, at least one bacterial strain of *Faecalibacterium prausnitzii* selected from the group consisting of bacterial strains deposited to the CNCM under the accession numbers I-4542, I-4544, I-4540, I-4574, I-4543, I-4575, I-4573, I-4644 and I-4546.

Preferably, a composition according to the invention comprises at least one bacterial strain deposited to the CNCM under the accession number I-4573.

A composition according to the invention is intended for the gastrointestinal tract, in particular the gut.

Consequently, a composition according to the invention is selected from an oral, rectal or parenteral composition. A composition of the invention is preferably an oral or rectal composition, more preferably an oral composition.

According to an embodiment, a composition of the invention is an oral composition, i.e. is intended for oral administration to a subject.

Such composition can be in the form of a suspension, tablet, pill, capsule, granulate or powder.

The composition according to the invention for the oral route can be selected from the group consisting of a food product, a drink, a pharmaceutical, a nutraceutical, a food additive, a food supplement or a dairy product, and is in particular a food supplement.

According to a preferred embodiment, a composition according to the invention is a food supplement.

Food supplement for oral administration may be present in capsules, gelatin capsules, soft capsules, tablets, sugar-coated tablets, pills, pastes, pastilles, gums, drinkable solutions or emulsions, a syrup or a gel.

Advantageously, a composition according to the invention, intended for oral administration, can be provided with a coating resistant to gastric juice, so as to ensure that the bacterial strain of the invention comprised in said composition can pass through the stomach undamaged. The release of the bacterial strain can thus takes place for the first time in the upper intestinal tract.

A food supplement according to the invention can also include a sweetener, a stabilizer, an antioxidant, an additive, a flavouring agent and/or a colorant.

The formulation thereof is carried out by means of the usual methods for producing sugar-coated tablets, gel capsules, gels, hydrogels for controlled release, emulsions, tablets or capsules.

A composition according to the invention can also be in the form of a nutritional composition.

A nutritional composition according to the invention is in the form of a yogurt, a cereal bar, a breakfast cereal, a dessert, a frozen food, a soup, a pet food, a liquid suspension, a powder, a tablet, a gum or a candy.

In a further embodiment of the invention, a composition containing a bacterial strain of the invention is administered intrarectally.

A rectal administration preferably takes place in the form of a suppository, enema or foam.

A composition according to the invention contains an amount of bacterial strains of the invention equivalent to between $10^3$ and $10^{12}$ cfu/g (dry weight basis), more preferably between $10^6$ and $10^9$ cfu/g.

A composition according to the invention can further comprise at least one of: antioxidants, fish oils, DHA, EPA, vitamins, minerals, phytonutrients, protein, fat, probiotics, and combinations thereof.

The present invention further concerns the use of at least one bacterial strain of the *Faecalibacterium prausnitzii* species selected from a bacterial strain belonging to at least one of the phylogroups I, II and III, for the treatment and/or prevention of visceral abdominal pain in an individual.

The present invention also concerns the use of a composition, preferably an oral composition, comprising, in a physiologically acceptable medium, at least one bacterial strain of the *Faecalibacterium prausnitzii* species selected from a bacterial strain belonging to at least one of the phylogroups I, II and III, for the treatment and/or prevention of visceral abdominal pain in an individual.

The invention will be described below in greater details using the following examples which are given for illustrative purposes only.

All references to percentages are percentages by weight unless otherwise stated.

Examples

*F. prausnitzii* strains according to the invention have been tested for their ability to have a direct impact on visceral pain, and more particularly on colonic hypersensitivity.

Bacterial Strains Isolation and Growth Conditions

The *F. prausnitzii* strains isolates used in the present example all are of human fecal origin from healthy patients. Said isolates were obtained from the highest countable dilution of human fecal samples in roll tubes of anaerobic M2GSC medium as discussed in Lopez-Siles et al. (Appl. Environ Microbiol. 2012; 78:420-428).

Tested *F. prausnitzii* strains isolates were grown in LYBHI medium (Brain-Heart infusion medium supplemented with 0.5% yeast extract) (Dyfco, Detroit, USA) supplemented with 1 mg/mL cellobiose (Sigma-Aldrich Chemie Gmbh, Buchs, Switzerland), 1 mg/mL maltose (Sigma-Aldrich) and 0.5 mg/mL cysteine (Sigma-Aldrich) at 37° C. in anaerobic chamber.

A. In a first series of tests, a Neonatal Maternal Separation (NMS) colonic hypersensitivity (CHS) mouse model is used.

a. NMS CHS Mouse Model

Pregnant C57B1/6J mice have been purchased from Janvier laboratories (Le Genest Saint Isle, France).

After birth, wild-type C57B1/6J were isolated from their mother from D2 to D14, three hours a day, from 9 a.m. to 12 a.m. At nine-week old age, male mice were orally treated each day for nine days with 200 µL of $10 \times 10^{10}$ CFU/mL of:
the strain CNCM I-4573 according to the invention;
the strain CNCM I-4541 outside the invention; or
PBS as control.

All the experiments were performed on the last day of treatment at D10.

The same bacteria treatment was administered to non-NMS CHS mice as a control.

NMS treatment induced an increased Vicero Motrice Response (VMR) in the absence of any significant alteration in gut wall macroscopic integrity or colonic mucosa inflammation (Coutinho et al. (2002), Am. J. Physiol. Gastrointest. Liver Physiol. 282(2): G307-16).

As described in Christianson et al. 2007 (Nat Protoc 2(10): 2624-31), colonic sensitivity was assessed by quantifying visceromotor response with abdominal electromyography (EMG) recordings in response to colorectal distension.

The inventors also validated this model as being non-inflammatory by checking the cytokines pattern by measurement of 13 types of cytokines in serum samples of stressed (MS: Maternal separated) and non-stressed (NH: Non-handled) mice.

It was observed that there are no differences in cytokine pattern induced by the chronic stress.

Moreover, NMS does not induce changes in colonic macroscopic damage, loss of architectural epithelium, goblet cell depletion, oedema/ulceration or inflammatory cell infiltrates.

Furthermore, NMS does not induce changes in body weight, colon weight and length and in spleen weight when stressed (MS) mice are compared to the control group (PBS).

b. Statistical Analysis

Statistical analysis was completed using GraphPad software (GraphPad Software, La Jolla, Calif., USA). All data were expressed as mean+/−SEM.

MS mice displaying VMR values lower than mean minus two SEM for all distension volumes were considered as non-sensitized and excluded from the analysis.

For VMR analysis in model validation, a two-way (Volume & Treatment) ANOVA followed by Bonferroni post-hoc test for multiple comparisons was used.

$P<0.05$ was considered statistically significant.

c. Results

Figure 1A:
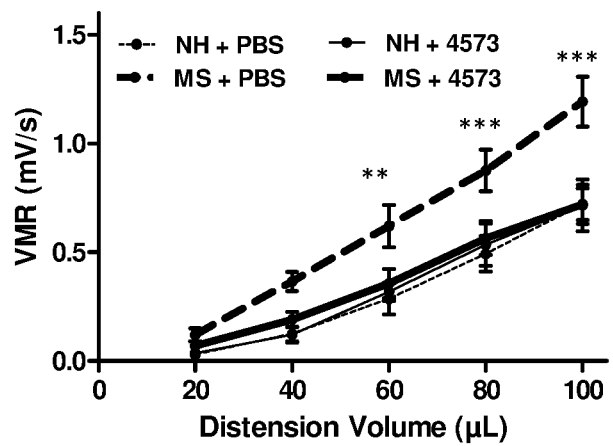
FIG. 1A illustrates the variation of the Vicero Motrice Response (VMR—mV/s) of a colon depending on the Distension volume (µL) of a balloon inserted into the rectum and slowly inflated, in non-handled (NH) (normal lines) or Maternal separated (MS) (bold lines) mice pre-treated with PBS (dotted lines) or with CNCM I-4573 (full lines) bacteria according to the invention.
Figure 1B:
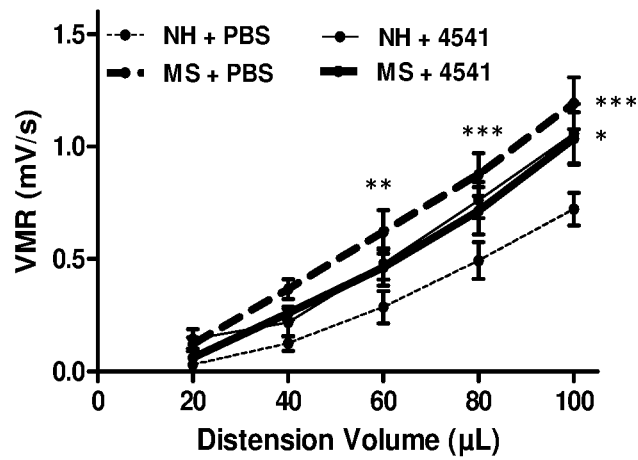
FIG. 1B illustrates the variation of the Vicero Motrice Response (VMR—mV/s) of a colon depending on the Distension volume (µL) of a balloon inserted into the rectum and slowly inflated, in non-handled (NH) (normal lines) or Maternal separated (MS) (bold lines) mice pre-treated with PBS (dotted lines) or with CNCM I-4541 (full lines) bacteria outside of the invention.

The results obtained are presented in FIGS. 1A and 1B.

As it can be seen in FIG. 1A, control Maternal separated (MS) mice, to whom only PBS was administered, present a high VMR, two times higher than the VMR of the non-handled (NH) mice, treated with CNCM I-4573 bacteria or only with PBS.

More importantly, it can be seen that MS mice to whom CNCM I-4573 bacteria of the invention were administered possess a VMR statistically similar to the one of NH mice, all along the growth of the Volume Distension.

On the contrary, in FIG. 1B, there is no statistical difference between the results obtained with MS mice only treated with PBS or treated with CNCM I-4541 bacteria.

Treatment based on the administration of *F. prausnitzii* strain CNCM I-4573 according to the invention led to a specific and significant decrease of the VMR in the tested mice as well as a prevention of the increase of the VMR.

On the contrary, the treatments based on the control tests (NH mice) and on the administration of *F. prausnitzii* strain CNCM I-4541 present no effect on the VMR of all the tested mice.

The present results clearly demonstrate that *F. prausnitzii* strains according to the invention have a specific and unexpected beneficial effect on visceral abdominal pain.

B. In a second series of tests, a Partial Restraint Stress (PRS) rat model is used.

a. Partial Restraint Stress (PRS) Rat Model

Animal preparation was performed as previously described in Ait-Belgnaoui et al.; Gut 55, 1090-1094 (2006).

Briefly, under general anesthesia induced by i.p. administration of 0.6 mg/kg acepromazine (Calmivet, Vetoquinol, Lure, France) and 120 mg/kg ketamine (Imalgene 1000, Merial, Lyon, France), female Wistar rats (Rosztóczy, A. et al.; Neurogastroenterol. Motil. Off. J. Eur. Gastrointest. Motil. Soc. 15, 679-686 (2003)) were equipped with three groups of three NiCr wire electrodes (60 cm in length, 80 nm in diameter) implanted into the abdominal external oblique muscle, 2 cm above the inguinal ligament.

Electrodes were exteriorized at the neck level by a glass tube attached to the skin.

During the ten days previous to the stress, 1 ml of $\pm 1 \times 10^9$ CFU or PBS were daily intragastrically administrated.

The study groups are as follows:
the strain CNCM I-4573 according to the invention;
the strain CNCM I-4541 outside the invention; or
PBS as control.

All stress sessions were performed at the same time of the day (between 10 am and 12 pm) to minimize any influence of circadian rhythms Stresses were performed using the wrap partial restrain stress model which is a mild non-ulcerogenic stressor (Williams, C. L et al.; Am. J. Physiol. 253, G582-586 (1987)).

Animals were lightly anesthetized (as previously described in Lee B. et al.; J. Neurogastroenterol. Motil. 17, 252-266 (2011), with ethyl-ether and their fore shoulders, upper forelimbs and thoracic trunk were draped in a confining harness of paper tape to restrict, but not to prevent, body movements.

Then rats were placed in their home cage for 2 h.

b. Rectal or Colorectal Distension and Colonic Hypersensitivity Measurement

Rats colonic sensitivity induced by PRS was assessed by quantifying electrical response through an electroencephalograph Reega Mini-hui (ALVAR, France) and expressed as number of abdominal cramps for a five min period (as previously described in Eutamene, H. et al.; J. Physiol. 506 (Pt 1), 245-252 (1998)).

Briefly, rats were accustomed to be in polypropylene tunnels (diameter 7 cm, length 20 cm) several days before colorectal distension (CRD) in order to minimize recording artifacts.

CRD was performed with an arterial embolectomy catheter (Fogarty; Edwards Laboratoire, Inc., Santa Ana, Calif., USA) introduced into the rectum (1 cm from the anus) and fixed at the base of the tail.

Distension of the colon was performed by connecting the catheter to a syringe and consecutive injections of different volumes (0.4, 0.8, 1.2 ml) with an interval of 5 minutes.

Each animal was recorded two days before the stress (basal measure) and just after the PRS (stress measure).

c. Statistical Analysis.

Statistical analysis was completed using GraphPad software (GraphPad Software, La Jolla, Calif., USA).

Results are presented with means±SEM.

Differences in the number of abdominal cramps during 5 minutes to gradual CRD volumes were analyzed using a 2-way ANOVA (Treatment, Volume) followed by Bonferroni post-hoc test for multiple comparisons.

A p value of less than 0.05 was considered significant.

d. Results

To determine if *F. prausnitzii* CNCMI-4541 (outside of the invention) and CNCMI-4573 (according to the invention) strains are able to prevent acute stress generated symptoms on visceral sensitivity, both were tested on a model of Partial Restraint Stress (PRS).

PRS increased the number of abdominal cramps in response to CRD in a volume-dependent manner (FIGS. 3A and 3B).

In stressed rats treated with PBS, distensions at any volumes significantly increased the number of abdominal contractions compared to non-stressed animals (p<0.01) (FIGS. 3A and 3B).

*F. prausnitzii* CNCMI-4573 strain treatment prevented this stress-induced visceral hypersensitivity until 0.8 ml distension volume (p<0.001) (FIG. 3A).

In basal conditions, no difference was observed in the VMR to CRD between the different treatments (FIG. 3A).

In contrast, *F. prausnitzii* CNCMI-4541 strain did not show a protective effect (FIG. 3B).

In conclusion, it appears that a *F. prausnitzii* strain according to the invention prevents visceral hypersensitivity in a model of Partial Restraint Stress (PRS).

```
SEQ ID No: 1: 16S rRNA sequence of
F. prausnitzii CNCM I-4540
AGAGTTTGATCCTGGCTCAGGACGAACGCTGGCGGCGCGCCTAACACA

TGCAAGTCGAACGAGTGAGAGAGAGCTTGCTTTCTCGAGCGAGTGGCG

AACGGGTGAGTAACGCGTGAGGAACCTGCCTCAAAGAGGGGACAACA

GTTGGAAACGACTGCTAATACCGCATAAGCCCACGGCTCGGCATCGAG

CAGAGGGAAAAGGAGTGATCCGCTTTGAGATGGCCTCGCGTCCGATTA

GCTAGTTGGTGAGGTAATGGCCCACCAAGGCGACGATCGGTAGCCGGA

CTGAGAGGTTGAACGGCCACATTGGGACTGAGACACGGCCCAGACTCC

TACGGGAGGCAGCAGTGGGGAATATTGCACAATGGGGGAAACCCTGAT

GCAGCGACGCCGCGTGGAGGAAGAAGGTCTTCGGATTGTAAACTCCTG
```

```
-continued
TTGTTGGGGAAGATAATGACGGTACCCAACAAGGAAGTGACGGCTAAC

TACGTGCCAGCAGCCGCGGTAAAACGTAGGTCACAAGCGTTGTCCGGA

ATTACTGGGTGTAAAGGGAGCGCAGGCGGGGAGACAAGTTGGAAGTGA

AATCTATGGGCTCAACCCATAAACTGCTTTCAAAACTGTTTTTCTTGA

GTAGTGCAGAGGTAGGCGGAATTCCCGGTGTAGCGGTGGAATGCGTAG

ATATCGGGAGGAACACCAGTGGCGAAGGCGGCCTACTGGGCACCAACT

GACGCTGAGGCTCGAAAGTGTGGGTAGCAAACAGGATTAGATACCCTG

GTAGTCCACACCGTAAACGATGATTACTAGGTGTTGGAGGATTGACCC

CTTCAGTGCCGCAGTTAACACAATAAGTAATCCACCTGGGGAGTACGA

CCGCAAGGTTGAAACTCAAAGGAATTGACGGGGGCCCGCACAAGCAGT

GGAGTATGTGGTTTAATTCGACGCAACGCGAAGAACCTTACCAAGTCT

TGACATCCCTTGACAGACATAGAAATATGTATTCTCTTCGGAGCAAGG

AGACAGGTGGTGCATGGTTGTCGTCAGCTCGTGTCGTGAGATGTTGGG

TTAAGTCCCGCAACGAGCGCAACCCTTATGGTCAGTTACTACGCAAGA

GGACTCTGGCCAGACTGCCGTTGACAAAACGGAGGAAGGTGGGGATGA

CGTCAAATCATCATGCCCTTTATGACTTGGGCTACACACGTACTACAA

TGGCGTTAAACAAAGAGAAGCAAGACCGCGAGGTGGAGCAAAACTCAG

AAACAACGTCCCAGTTCGGACTGCAGGCTGCAACTCGCCTGCACGAAG

TCGGAATTGCTAGTAATCGTGGATCAGCATGCCACGGTGAATACGTTC

CCGGGCCTTGTACACACCGCCCGTCACACCATGAGAGCCGGGGGGACC

CGAAGTCGGTAGTCTAACCGCAAGGAGGACGCCGCCGAAGGTAAAACT

GGTGATTGGGGTGAAGTCGTAACAAGGTAGCCGT

SEQ ID No: 2: 16S rRNA sequence of
F. prausnitzii CNCM I-4542
AGAGTTTGATCCTGGCTCAGGACGAACGCTGGCGGCGCGCCTAACACA

TGCAAGTCGAACGAGCGAGAGAGAGCTTGCTTTCTCGAGCGAGTGGCG

AACGGGTGAGTAACGCGTGAGGAACCTGCCTCAAAGAGGGGACAACA

GTTGGAAACGACTGCTAATACCGCATAAGCCCACGGGTCGGCATCGAC

CAGAGGGAAAAGGAGCAATCCGCTTTGAGATGGCCTCGCGTCCGATTA

GCTAGTTGGTGAGGTAATGGCCCACCAAGGCAACGATCGGTAGCCGGA

CTGAGAGGTTGAACGGCCACATTGGGACTGAGACGCGGCCCAGACTCC

TACGGGAGGCAGCAGTGGGGAATATTGCACAATGGGGGAAACCCTGAT

GCAGCGACGCCGCGTGGAGGAAGAAGGTCTTCGGATTGTAAACTCCTG

TTGTTGGGGAAGATAATGACGGTACCCAACAAGGAAGTGACGGCTAAC

TACGTGCCAGCAGCCGCGGTAAAACGTAGGTCACAAGCGTTGTCCGGA

ATTACTGGGTGTAAAGGGAGCGCAGGCGGGAAGACAAGTTGGAAGTGA

AATCTATGGGCTCAACCCATAAACTGCTTTCAAAACTGTTTTTCTTGA

GTAGTGCAGAGGTAGGCGGAATTCCCGGTGTAGCGGTGGAATGCGTAG

ATATCGGGAGGAACACCAGTGGCGAAGGCGGCCTACTGGGCACCAACT

GACGCTGAGGCTCGAAAGTGTGGGTAGCAAACAGGATTAGATACCCTG

GTAGTCCACACCGTAAACGATGGTTACTAGGTGTTGGAGGATTGACCC

CTTCAGTGCCGCAGTTAACACAATAAGTAATCCACCTGGGGAGTACGA
```

-continued

CCGCAAGGTTGAAACTCAAAGGAATTGACGGGGGCCCGCACAAGCAGT

GGAGTATGTGGTTTAATTCGACGCAACGCGAAGAACCTTACCAAGTCT

TGACATCCCTTGACAGACATAGAAATATGTAATCTCTTCGGAGCAAGG

AGACAGGTGGTGCATGGTTGTCGTCAGCTCGTGTCGTGAGATGTTGGG

TTAAGTCCCGCAACGAGCGCAACCCTTATGGTCAGTTACTACGCAAGA

GGACTCTGGCCAGACTGCCGTTGACAAAACGGAGGAAGGTGGGGATGA

CGTCAAATCATCATGCCCTTTATGACTTGGGCTACACACGTACTACAA

TGGCGTTAAACAAAGAGAAGCAAGACCGCGAGGTGGAGCAAAACTCAG

AAACAACGTCCCAGTTCGGACTGCAGGCTGCAACTCGCCTGCACGAAG

TCGGAATTGCTAGTAATCGTGGATCAGCATGCCACGGTGAATACGTTC

CCGGGCCTTGTACACACCGCCCGTCACACCATGAGAGCCGGGGGACC

CGAAGTCGGTAGTCTAACCGCAAGGAGGACGCCGCCGAAGGTAAAACT

GGTGATTGGGGTGAAGTCGTAACAAGGTAGCCGT

SEQ ID No: 3: 16S rRNA sequence of
F. prausnitzii S3C12
GCGAGAGAGAGCTTGCTTTCTCGAGCGAGTGGCGAACGGGTGAGTAAC

GCGTGAGGAACCTGCCTCAAAGAGGGGGACAACAGTTGGAAACGACTG

CTAATACCGCATAAGCCCACGGCCCGGCATCGGGCAGAGGGAAAAGGA

GCAATCCGCTTTGAGATGGCCTCGCGTCCGATTAGCTAGTTGGTGAGG

TAACGGCCCACCAAGGCGACGATCGGTAGCCGGACTGAGAGGTTGAAC

GGCCACATTGGGACTGAGACACGGCCCAGACTCCTACGGGAGGCAGCA

GTGGGGAATATTGCACAATGGGGGAAACCCTGATGCAGCGACGCCGCG

TGGAGGAAGAAGGTCTTCGGATTGTAAACTCCTGTTGTTGAGGAAGAT

AATGACGGTACTCAACAAGGAAGTGACGGCTAACTACGTGCCAGCAGC

CGCGGTAAAACGTAGGTCACAAGCGTTGTCCGGAATTACTGGGTGTAA

AGGGAGCGCAGGCGGGAAGACAAGTTGGAAGTGAAATCCATGGGCTCA

ACCCATGAACTGCTTTCAAAACTGTTTTTCTTGAGTAGTGCAGAGGTA

GGCGGAATTCCCGGTGTAGCGGTGGAATGCGTAGATATCGGGAGGAAC

ACCAGTGGCGAAGGCGGCCTACTGGGCACCAACTGACGCTGAGGCTCG

AAAGTGTGGGTAGCAAACAGGATTAGATACCCTGGTAGTCCACACCGT

AAACGATGATTACTAGGTGTTGGAGGATTGACCCCTTCAGTGCCGCAG

TTAACACAATAAGTAATCCACCTGGGGAGTACGACCGCAAGGTTGAAA

CTCAAAGGAATTGACGGGGGCCCGCACAAGCAGTGGAGTATGTGGTTT

AATTCGACGCAACGCGAAGAACCTTACCAAGTCTTGACATCCTGCGAC

GGTTCTGGAAACAGAACTTTCCTTCGGGACGCAGAGACAGGTGGTGCA

TGGTTGTCGTCAGCTCGTGTCGTGAGATGTTGGGTTAAGTCCCGCAAC

GAGCGCAACCCTTATGGTCAGTTACTACGCAAGAGGACTCTGGCCAGA

CTGCCGTTGACAAAACGGAGGAAGGTGGGGATGACGTCAAATCATCAT

GCCCTTTATGACTTGGGCTACACACGTACTACAATGGCGTTAAACAAA

GAGAAGCAAGACCGCGAGGTGGAGCAAAACTCAGAAACAACGTCCCAG

TTCGGACTGCAGGCTGCAACTCGCCTGCACGAAGTCGGAATTGCTAGT

AATCGTGGATCAGCATGCCACGGTGAATACGTTCCCGGGCCTTGTACA

CACCGCCCGTCACACCATGAGAGCCGGGGGACCCGAAGTCGGTAGTC

TAACCGCAAGGAGGACGCCGCCGAAGGTAAAACTGGTGATTGGGGTGA

AGTCGTAACAAGGTAG

SEQ ID No: 4: 16S rRNA sequence of
F. prausnitzii S3G1
AGCGAGAGAGAGCTTGCTTTCTCGAGCGAGTGGCGAACGGGTGAGTAA

CGCGTGAGGAACCTGCCTCAAAGAGGGGGACAACAGTTGGAAACGACT

GCTAATACCGCATAAGCCCACGGTGCCGCATGGCACAGAGGGAAAAGG

AGCAATCCGCTTTGAGATGGCCTCGCGTCCGATTAGCTAGTTGGTGAG

GTAACGGCCCACCAAGGCGACGATCGGTAGCCGGACTGAGAGGTTGAA

CGGCCACATTGGGACTGAGACACGGCCCAGACTCCTACGGGAGGCAGC

AGTGGGGAATATTGCACAATGGGGGAAACCCTGATGCAGCGACGCCGC

GTGGAGGAAGAAGGTCTTCGGATTGTAAACTCCTGTTGTTGGGGAAGA

TAATGACGGTACCCAACAAGGAAGTGACGGCTAACTACGTGCCAGCAG

CCGCGGTAAAACGTAGGTCACAAGCGTTGTCCGGAATTACTGGGTGTA

AAGGGAGCGCAGGCGGGAAGACAAGTTGGAAGTGAAATCTATGGGCTC

AACCCATAAACTGCTTTCAAAACTGTTTTTCTTGAGTAGTGCAGAGGT

AGGCGGAATTCCCGGTGTAGCGGTGGAATGCGTAGATATCGGGAGGAA

CACCAGTGGCGAAGGCGGCCTACTGGGCACCAACTGACGCTGAGGCTC

GAAAGTGTGGGTAGCAAACAGGATTAGATACCCTGGTAGTCCACACCG

TAAACGATGATTACTAGGTGTTGGAGGATTGACCCCTTCAGTGCCGCA

GTTAACACAATAAGTAATCCACCTGGGGAGTACGACCGCAAGGTTGAA

ACTCAAAGGAATTGACGGGGGCCCGCACAAGCAGTGGAGTATGTGGTT

TAATTCGACGCAACGCGAAGAACCTTACCAAGTCTTGACATCCCTTGA

CAGGCATAGAAATATGTTTTCTCTTCGGAGCAAGGAGACAGGTGGTGC

ATGGTTGTCGTCAGCTCGTGTCGTGAGATGTTGGGTTAAGTCCCGCAA

CGAGCGCAACCCTTATGGTCAGTTACTACGCAAGAGGACTCTGGCCAG

ACTGCCGTTGACAAAACGGAGGAAGGTGGGGATGACGTCAAATCATCA

TGCCCTTTATGACTTGGGCTACACACGTACTACAATGGCGTTAAACAA

AGAGAAGCAAGACCGCGAGGTGGAGCAAAACTCAGAAACAACGTCCCA

GTTCGGACTGCAGGCTGCAACTCGCCTGCACGAAGTCGGAATTGCTAG

TAATCGTGGATCAGCATGCCACGGTGAATACGTTCCCGGGCCTTGTAC

ACACCGCCCGTCACACCATGAGAGCCGGGGGACCCGAAGTCGGTAGT

CTAACCGCAAGGAGGACGCCGCCGAAGGTAAAACTGGTGATTGGGGTG

AAGTCGTAACAAG

SEQ ID No: 5: 16S rRNA sequence of
F. prausnitzii CNCM I-4574
CGAGTGGCGAACGGGTGAGTAACGCGTGAGGAACCTGCCTCAAAGAGG

GGGACAACAGTTGGAAACGACTGCTAATACCGCATAAGCCCACAGGTC

GGCATCGACCAGAGGGAAAAGGAGCAATCCGCTTTGAGATGGCCTCGC

GTCCGATTAGCTAGTTGGTGAGGTAATGGCCCACCAAGGCAACGATCG

GTAGCCGGACTGAGAGGTTGAACGGCCACATTGGGACTGAGACACGGC

CCAGACTCCTACGGGAGGCAGCAGTGGGGAATATTGCACAATGGGGGA
AACCCTGATGCAGCGACGCCGCGTGGAGGAAGAAGGTCTTCGGATTGT
AAACTCCTGTTGTTGAGGAAGATAATGACGGTACTCAACAAGGAAGTG
ACGGCTAACTACGTGCCAGCAGCCGCGGTAAAACGTAGGTCACAAGCG
TTGTCCGGAATTACTGGGTGTAAAGGGAGCGCAGGCGGGAAGACAAGT
TGGAAGTGAAATCTATGGGCTCAACCCATAAACTGCTTTCAAAACTGT
TTTTCTTGAGTAGTGCAGAGGTAGGCGGAATTCCCGGTGTAGCGGTGG
AATGCGTAGATATCGGGAGGAACACCAGTGGCGAAGGCGGCCTACTGG
GCACCAACTGACGCTGAGGCTCGAAAGTGTGGGTAGCAAACAGGATTA
GATACCCTGGTAGTCCACACCGTAAACGATGATTACTAGGTGTTGGAG
GATTGACCCCTTCAGTGCCGCAGTTAACACAATAAGTAATCCACCTGG
GGAGTACGACCGCAAGGTTGAAACTCAAAGGAATTGACGGGGCCCGC
ACAAGCAGTGGAGTATGTGGTTTAATTCGACGCAACGCGAAGAACCTT
ACCAAGTCTTGACATCCTGTGACGATGCTGGAAACATGTTTTTCCTTC
GGAACGCAGAGACAGGTGGTGCATGGTTGTCGTCAGCTCGTGTCGTGA
GATGTTGGGTTAAGTCCCGCAACGAGCGCAACCCTTACTGTCAGTTAC
TACGCAAGAGGACTCTGGCAGGACTGCCGTTGACAAAACGGAGGAAGG
TGGGGATGACGTCAAATCATCATGCCCTTTATGACTTGGGCTACACAC
GTACTACAATGGCGTTAAACAAAGAGAAGCAAGACCGCGAGGTGGAGC
AAAACTCAGAAACAACGTCCCAGTTCGGACTGCAGGCTGCAACTCGCC
TGCACGAAGTCGGAATTGCTAGTAATCGTGGATCAGCATGCCACGGTG
AATACGTTCCCGGGCCTTGTACACACCGCCCGTCACACCATGAGAGCC
GGGGGGACCCGAAGTCGGTAGTCTAACCGCAAGGAGGACGCCGCCGAA
GGTAAAACTGGTGATTGGGGTGAAGTCGTAACAAGGTAGCC

SEQ ID No: 6: 16S rRNA sequence of
F. prausnitzii CNCM I-4543
CGAGCGAGAGAGAGCTTGCTTTCTCAATCGAGTGGCGAACGGGTGAGT
AACGCGTGAGGAACCTGCCTCAAAGAGGGGGACAACAGTTGGAAACGA
CTGCTAATACCGCATAAGCCCACAGGTCGGCATCGACCAGAGGGAAAA
GGAGCAATCCGCTTTGAGATGGCCTCGCGTCCGATTAGCTAGTTGGTG
AGGTAATGGCCCACCAAGGCAACGATCGGTAGCCGGACTGAGAGGTTG
AACGGCCACATTGGGACTGAGACACGGCCCAGACTCCTACGGGAGGCA
GCAGTGGGGAATATTGCACAATGGGGGAAACCCTGATGCAGCGACGCC
GCGTGGAGGAAGAAGGTCTTCGGATTGTAAACTCCTGTTGTTGAGGAA
GATAATGACGGTACTCAACAAGGAAGTGACGGCTAACTACGTGCCAGC
AGCCGCGGTAAAACGTAGGTCACAAGCGTTGTCCGGAATTACTGGGTG
TAAAGGGAGCGCAGGCGGGAAGACAAGTTGGAAGTGAAATCTATGGGC
TCAACCCATAAACTGCTTTCAAAACTGTTTTTCTTGAGTAGTGCAGAG
GTAGGCGGAATTCCCGGTGTAGCGGTGGAATGCGTAGATATCGGGAGG
AACACCAGTGGCGAAGGCGGCCTACTGGGCACCAACTGACGCTGAGGC
TCGAAAGTGTGGGTAGCAAACAGGATTAGATACCCTGGTAGTCCACAC
CGTAAACGATGATTACTAGGTGTTGGAGGATTGACCCCTTCAGTGCCG
CAGTTAACACAATAAGTAATCCACCTGGGGAGTACGACCGCAAGGTTG
AAACTCAAAGGAATTGACGGGGCCCGCACAAGCAGTGGAGTATGTGG
TTTAATTCGACGCAACGCGAAGAACCTTACCAAGTCTTGACATCCTGT
GACGAACCTGGAAATATGTTTTTCCTTCGGAACGCAGAGACAGGTGGT
GCATGGTTGTCGTCAGCTCGTGTCGTGAGATGTTGGGTTAAGTCCCGC
AACGAGCGCAACCCTTACTGTCAGTTACTACGCAAGAGGACTCTGGCA
GGACTGCCGTTGACAAAACGGAGGAAGGTGGGGATGACGTCAAATCAT
CATGCCCTTTATGACTTGGGCTACACACGTACTACAATGGCGTTAAAC
AAAGAGAAGCAAGACCGCGAGGTGGAGCAAAACTCAGAAACAACGTCC
CAGTTCGGACTGCAGGCTGCAACTCGCCTGCACGAAGTCGGAATTGCT
AGTAATCGTGGATCAGCATGCCACGGTGAATACGTTCCCGGGCCTTGT
ACACACCGCCCGTCACACCATGAGAGCCGGGGGGACCCGAAGTCGGTA
GTCTAACCGCAAGGAGGACGCCGCCGAAGGTAAAACTGGTGATTGGGG
TGAAGTCGTACAG SEQ ID No: 7: 16S rRNA sequence of
F. prausnitzii S9D8
AGAGTTTGATCCTGGCTCAGGACGAACGCTGGCGGCGCGCCTAACACA
TGCAAGTCGAACGAGCGAGAGAGAGCTTGCTTTCTCGAGCGAGTGGCG
AACGGGTGAGTAACGCGTGGGGAACCTGCCTCAAAGAGGGGGACAACA
GTTGGAAACGACTGCTAATACCGCATAAGCCCACGACCTGGCATCGGG
TTGAGGGAAAAGGAGCAATCCGCTTTGAGATGGCCTCGCGTCCGATTA
GCTAGTTGGTGAGGTAATGGCCCACCAAGGCAACGATCGGTAGCCGGA
CTGAGAGGTTGAACGGCCACATTGGGACTGAGACACGGCCCAGACTCC
TACGGGAGGCAGCAGTGGGGAATATTGCACAATGGGGGAAACCCTGAT
GCAGCGACGCCGCGTGGAGGAAGAAGGTCTTCGGATTGTAAACTCCTG
TTGTTGAGGAAGATAATGACGGTACTCAACAAGGAAGTGACGGCTAAC
TACGTGCCAGCAGCCGCGGTAAAACGTAGGTCACAAGCGTTGTCCGGA
ATTACTGGGTGTAAAGGGAGCGCAGGCGGGAAGACAAGTTGGAAGTGA
AATCCATGGGCTCAACCCATGAACTGCTTTCAAAACTGTTTTTCTTGA
GTAGTGCAGAGGTAGGCGGAATTCCCGGTGTAGCGGTGGAATGCGTAG
ATATCGGGAGGAACACCAGTGGCGAAGGCGGCCTACTGGGCACCAACT
GACGCTGAGGCTCGAAAGTGTGGGTAGCAAACAGGATTAGATACCCTG
GTAGTCCACACCGTAAACGATGATTACTAGGTGTTGGAGGATTGACCC
CTTCAGTGCCGCAGTTAACACAATAAGTAATCCACCTGGGGAGTACGA
CCGCAAGGTTGAAACTCAAAGGAATTGACGGGGCCCGCACAAGCAGT
GGAGTATGTGGTTTAATTCGACGCAACGCGAAGAACCTTACCAAGTCT
TGACATCCTGCGACGGTGCTGGAAACAGTGCTTTCCTTCGGGACGCAG
AGACAGGTGGTGCATGGTTGTCGTCAGCTCGTGTCGTGAGATGTTGGG
TTAAGTCCCGCAACGAGCGCAACCCTTATGGTCAGTTACTACGCAAGA
GGACTCTGGCCAGACTGCCGTTGACAAAACGGAGGAAGGTGGGGATGA
CGTCAAATCATCATGCCCTTTATGACTTGGGCTACACACGTACTACAA -continued

TGGCGTTAAACAAAGAGAAGCAAGACCGCGAGGTGGAGCAAAACTCAG

AAACAACGTCCCAGTTCGGACTGCAGGCTGCAACTCGCCTGCACGAAG

TCGGAATTGCTAGTAATCGTGGATCAGCATGCCACGGTGAATACGTTC

CCGGGCCTTGTACACACCGCCCGTCACACCATGAGAGCCGGGGGACC

CGAAGTCGGTAGTCTAACCGCAAGGAGGACGCCGCCGAAGGTAAAACT

GGTGATTGGGGTGAAGTCGTAACAAGGTAGCCGT

SEQ ID No: 8: 16S rRNA sequence of
F. prausnitzii S9G3
GCATGCTCGAGCGGCCGCCAGTGTGATGGATATCTGCAGAATTCGCCC

TTAGAGTTTGATCCTGGCTCAGGACGAACGCTGGCGGCGCGCCTAACA

CATGCAAGTCGAACGAGCGAGAGAGAGCTTGCTTTCTCGAGCGAGTGG

CGAACGGGTGAGTAACGCGTGAGGAACCTGCCTCAAAGAGGGGGACAA

CAGTTGGAAACGACTGCTAATACCGCATAAGCCCACGACCCGGCATCG

GGTAGAGGGAAAAGGAGCAATCCGCTTTGAGATGGCCTCGCGTCCGAT

TAGCTAGTTGGTGAGGTAACGGCCCACCAAGGCGACGATCGGTAGCCG

GACTGAGAGGTTGAACGGCCACATTGGGACTGAGACACGGCCCAGACT

CCTACGGGAGGCAGCAGTGGGGAATATTGCACAATGGGGGAAACCCTG

ATGCAGCGACGCCGCGTGGAGGAAGAAGGTCTTCGGATTGTAAACTCC

TGTTGTTGAGGAAGATAATGACGGTACTCAACAAGGAAGTGACGGCTA

ACTACGTGCCAGCAGCCGCGGTAAAACGTAGGTCACAAGCGTTGTCCG

GAATTACTGGGTGTAAAGGGAGCGCAGGCGGGAAGACAAGTTGGAAGT

GAAATCCATGGGCTCAACCCATGAACTGCTTTCAAAACTGTTTTTCTT

GAGTAGTGCAGAGGTAGGCGGAATTCCCGGTGTAGCGGTGGAATGCGT

AGATATCGGAGGAACACCAGTGGCGAAGGCGGCCTACTGGGCACCAA

CTGACGCTGAGGCTCGAAAGTGTGGGTAGCAAACAGGATTAGATACCC

TGGTAGTCCACACCGTAAACGATGATTACTAGGTGTTGGAGGATTGAC

CCCTTCAGTCCGCAGTTAACACAATAAGTAATCCACCTGGGGAGTAC

GACCGCAAGGTTGAAACTCAAAGGAATTGACGGGGGCCCGCACAAGCA

GTGGAGTATGTGGTTTAATTCGACGCAACGCGAAGAACCTTACCAAGT

CTTGACATCCTGCGACGGTTCTGGAAACAGAACTTTCCTTCGGGACGC

AGAGACAGGTGGTGCATGGTTGTCGTCAGCTCGTGTCGTGAGATGTTG

GGTTAAGTCCCGCAACGAGCGCAACCCTTATGGTCAGTTACTACGCAA

GAGGACTCTGGCCAGACTGCCGTTGACAAAACGGAGGAAGGTGGGGAT

GACGTCAAATCATCATGCCCTTTATGACTTGGGCTACACACGTACTAC

AATGGCGTTAAACAAAGAGAAGCAAGACCGCGAGGTGGAGCAAAACTC

AGAAACAACGTCCCAGTTCGGACTGCAGGCTGCAACTCGCCTGCACGA

AGTCGGAATTGCTAGTAATCGTGGATCAGCATGCCACGGTGAATACGT

TCCCGGGCCTTGTACACACCGCCCGTCACACCATGAGAGCCGGGGGA

CCCGAAGTCGGTAGTCTAACCGCAAGGAGGACGCCGCCGAAGGTAAAA

CTGGTGATTGGGGTGAAGTCGTAACAAGGTAGCCGTAAGGGCGAA

SEQ ID No: 9: 16S rRNA sequence of
F. prausnitzii CNCM I-4644
GCATCGGGCAGAGGGAAAAGGAGCAATCCGCTTTGAGATGGCCTCGCG

TCCGATTAGCTAGTTGGTGAGGTAATGGCCCACCAAGGCGACGATCGG

TAGCCGGACTGAGAGGTTGAACGGCCACATTGGGACTGAGACACGGCC

CAGACTCCTACGGGAGGCAGCAGTGGGGAATATTGCACAATGGGGGAA

ACCCTGATGCAGCGACGCCGCGTGGAGGAAGAAGGTCTTCGGATTGTA

AACTCCTGTTGTTGAGGAAGATAATGACGGTACTCAACAAGGAAGTGA

CGGCTAACTACGTGCCAGCAGCCGCGGTAAAACGTAGGTCACAAGCGT

TGTCCGGAATTACTGGGTGTAAAGGGAGCGCAGGCGGGAAGACAAGTT

GGAAGTGAAATCCATGGGCTCAACCCATGAACTGCTTTCAAAACTGTT

TTTCTTGAGTAGTGCAGAGGTAGGCGGAATTCCCGGTGTAGCGGTGGA

ATGCGTAGATATCGGAGGAACACCAGTGGCGAAGGCGGCCTACTGGG

CACCAACTGACGCTGAGGCTCGAAAGTGTGGGTAGCAAACAGGATTAG

ATACCCTGGTAGTCCACACTGTAAACGATGATTACTAGGTGTTGGAGG

ATTGACCCCTTCAGTGCCGCAGTTAACACAATAAGTAATCCACCTGGG

GAGTACGACCGCAAGGTTGAAACTCAAAGGAATTGACGGGGGCCCGCA

CAAGCAGTGGAGTATGTGGTTTAATTCGACGCAACGCGAAGAACCTTA

CCAAGTCTTGACATCCTGCGACGCACATAGAAATATGTGTTTCCTTCG

GGACGCAGAGACAGGTGGTGCATGGTTGTCGTCAGCTCGTGTCGTGAG

ATGTTGGGTTAAGTCCCGCAACGAGCGCAACCCTTATGGTCAGTTACT

ACGCAAGAGGACTCTGGCCAGACTGCCGTTGACAAAACGGAGGAAGGT

GCGAGGTGGAGCAAAACTCAGAAACAACGTCCCAGTTCGGACTGCAGG

GGGGATGACGTCAAATCATCATGCCCTTTATGACTTGGGCTACACACG

TACTACAATGGCGTTAAACAAAGAGAAGCAAGACCCTGCAACTCGCCT

GCACGAAGTCGGAATTGCTAGTAATCGCAGATCAGCATGCTGCGGTGA

ATACGTTCCCGGGCCTTGTACACACCGCCCGTCACACCATGAGAGCCG

GGGGGACCCGAAGTCGGTAGTCTAACCGCAAGGAGGACGCCGCCGAAG

GTAAAACTGGTGATTGGGGTGAAGTCGTAACAAGGTAG

SEQ ID No: 10: 16S rRNA sequence of
F. prausnitzii CNCM I-4544
CGAGCGAGAGAGAGCTTGCTTTCTCGAGCGAGTGGCGAACGGGTGAGT

AACGCGTGAGGAACCTGCCTCAAAGAGGGGGACAACAGTTGGAAACGA

CTGCTAATACCGCATAAGCCCACGGGTCGGCATCGACCAGAGGGAAAA

GGAGCAATCCGCTTTGAGATGGCCTCGCGTCCGATTAGCTAGTTGGTG

AGGTAACGGCCCACCAAGGCAACGATCGGTAGCCGGACTGAGAGGTTG

AACGGCCACATTGGGACTGAGACACGGCCCAGACTCCTACGGGAGGCA

GCAGTGGGGAATATTGCACAATGGGGGAAACCCTGATGCAGCGACGCC

GCGTGGAGGAAGAAGGTCTTCGGATTGTAAACTCCTGTTGTTGGGGAA

GATAATGACGGTACCCAACAAGGAAGTGACGGCTAACTACGTGCCAGC

AGCCGCGGTAAAACGTAGGTCACAAGCGTTGTCCGGAATTACTGGGTG

TAAAGGGAGCGCAGGCGGGAAGACAAGTTGGAAGTGAAATCTATGGGC

TCAACCCATAAACTGCTTTCAAAACTGTTTTTCTTGAGTAGTGCAGAG

GTAGGCGGAATTCCCGGTGTAGCGGTGGAATGCGTAGATATCGGGAGG

AACACCAGTGGCGAAGGCGGCCTACTGGGCACCAACTGACGCTGAGGC

TCGAAAGTGTGGGTAGCAAACAGGATTAGATACCCTGGTAGTCCACAC

CGTAAACGATGATTACTAGGTGTTGGAGGATTGACCCCTTCAGTGCCG

CAGTTAACACAATAAGTAATCCACCTGGGGAGTACGACCGCAAGGTTG

AAACTCAAAGGAATTGACGGGGCCCGCACAAGCAGTGGAGTATGTGG

TTTAATTCGACGCAACGCGAAGAACCTTACCAAGTCTTGACATCCCTT

GACAGACATAGAAATATGTAATCTCTTCGGAGCAAGGAGACAGGTGGT

GCATGGTTGTCGTCAGCTCGTGTCGTGAGATGTTGGGTTAAGTCCCGC

AACGAGCGCAACCCTTATGGTCAGTTACTACGCAAGAGGACTCTGGCC

AGACTGCCGTTGACAAAACGGAGGAAGGTGGGGATGACGTCAAATCAT

CATGCCCTTTATGACTTGGGCTACACACGTACTACAATGGCGTTAAAC

AAAGAGAAGCAAGACCGCGAGGTGGAGCAAAACTCAGAAACAACGTCC

CAGTTCGGACTGCAGGCTGCAACTCGCCTGCACGAAGTCGGAATTGCT

AGTAATCGTGGATCAGCATGCCACGGTGAATACGTTCCCGGGCCTTGT

ACACACCGCCCGTCACACCATGAGAGCCGGGGGGACCCGAAGTCGGTA

GTCTAACCGCAAGGAGGACGCCGCCGAAGGTAAAACTGGTGATTGGGG

TGAAGTCGTAACAAG

SEQ ID No: 11: 16S rRNA sequence of
F. prausnitzii S10H3
GAGCGAGTGGCGAACGGGTGAGTAACGCGTGAGGAACCTGCCTCAAAG

AGGGGGACAACAGTTGGAAACGACTGCTAATACCGCATAAGCCCACGA

CCCGGCATCGGGTAGAGGGAAAAGGAGCAATCCGCTTTGAGATGGCCT

CGCGTCCGATTAGCTAGTTGGTGAGGTAATGGCCCACCAAGGCGACGA

TCGGTAGCCGGACTGAGAGGTTGAACGGCCACATTGGGACTGAGACAC

GGCCCAGACTCCTACGGGAGGCAGCAGTGGGGAATATTGCACAATGGG

GGAAACCCTGATGCAGCGACGCCGCGTGGAGGAAGAAGGTCTTCGGAT

TGTAAACTCCTGTTGTTGAGGAAGATAATGACGGTACTCAACAAGGAA

GTGACGGCTAACTACGTGCCAGCAGCCGCGGTAAAACGTAGGTCACAA

GCGTTGTCCGGAATTACTGGGTGTAAAGGGAGCGCAGGCGGGAAGACA

AGTTGGAAGTGAAATCCATGGGCTCAACCCATGAACTGCTTTCAAAAC

TGTTTTTCTTGAGTAGTGCAGAGGTAGGCGGAATTCCCGGTGTAGCGG

TGGAATGCGTAGATATCGGGAGGAACACCAGTGGCGAAGGCGGCCTAC

TGGGCACCAACTGACGCTGAGGCTCGAAAGTGTGGGTAGCAAACAGGA

TTAGATACCCTGGTAGTCCACACTGTAAACGATGATTACTAGGTGTTG

GAGGATTGACCCCTTCAGTGCCGCAGTTAACACAATAAGTAATCCACC

TGGGGAGTACGACCGCAAGGTTGAAACTCAAAGGAATTGACGGGGCC

CGCACAAGCAGTGGAGTATGTGGTTTAATTCGACGCAACGCGAAGAAC

CTTACCAAGTCTTGACATCCTGCGACGCACATAGAAATATGTGTTTCC

TTCGGGACGCAGAGACAGGTGGTGCATGGTTGTCGTCAGCTCGTGTCG

TGAGATGTTGGGTTAAGTCCCGCAACGAGCGCAACCCTTATGGTCAGT

TACTACGCAAGAGGACTCTGGCCAGACTGCCGTTGACAAAACGGAGGA

AGGTGGGGATGACGTCAAATCATCATGCCCTTTATGACTTGGGCTACA

CACGTACTACAATGGCGTTAAACAAAGAGAAGCAAGACCGCGAGGTGG

AGCAAAACTCAGAAACAACGTCCCAGTTCGGACTGCAGGCTGCAACTC

GCCTGCACGAAGTCGGAATTGCTAGTAATCGCAGATCAGCATGCTGCG

GTGAATACGTTCCCGGGCCTTGTACACACCGCCCGTCACACCATGAGA

GCCGGGGGGACCCGAAGTCGGTAGTCTAACCGCAAGGAGGACGCCGCC

GAAGGTAAAACTGGTGATTGGGGTGAAGTCGTAACAAG

SEQ ID No: 12: 16S rRNA sequence of
F. prausnitzii S13A7
AGCTTGCTTTCTCGAGCGAGTGGCGAACGGGTGAGTAACGCGTGAGGA

ACCTGCCTCAAAGAGGGGGACAACAGTTGGAAACGACTGCTAATACCG

CATAAGCCCACGGGTCGGCATCGACCAGAGGGAAAAGGAGCAATCCGC

TTTGAGATGGCCTCGCGTCCGATTAGCTAGTTGGTGAGGTAACGGCCC

ACCAAGGCGACGATCGGTAGCCGGACTGAGAGGTTGAACGGCCACATT

GGGACTGAGACACGGCCCAGACTCCTACGGGAGGCAGCAGTGGGGAAT

ATTGCACAATGGGGGAAACCCTGATGCAGCGACGCCGCGTGGAGGAAG

AAGGTCTTCGGATTGTAAACTCCTGTTGTTGGGGAAGATAATGACGGT

ACCCAACAAGGAAGTGACGGCTAACTACGTGCCAGCAGCCGCGGTAAA

ACGTAGGTCACAAGCGTTGTCCGGAATTACTGGGTGTAAAGGGAGCGC

AGGCGGGAAGACAAGTTGGAAGTGAAATCTATGGGCTCAACCCATAAA

CTGCTTTCAAAACTGTTTTTCTTGAGTAGTGCAGAGGTAGGCGGAATT

CCCGGTGTAGCGGTGGAATGCGTAGATATCGGGAGGAACACCAGTGGC

GAAGGCGGCCTACTGGGCACCAACTGACGCTGAGGCTCGAAAGTGTGG

GTAGCAAACAGGATTAGATACCCTGGTAGTCCACACCGTAAACGATGA

TTACTAGGTGTTGGAGGATTGACCCCTTCAGTGCCGCAGTTAACACAA

TAAGTAATCCACCTGGGGAGTACGACCGCAAGGTTGAAACTCAAAGGA

ATTGACGGGGCCCGCACAAGCAGTGGAGTATGTGGTTTAATTCGACG

CAACGCGAAGAACCTTACCAAGTCTTGACATCCCTTGACAGACATAGA

AATATGTATTCTCTTCGGAGCAAGGAGACAGGTGGTGCATGGTTGTCG

TCAGCTCGTGTCGTGAGATGTTGGGTTAAGTCCCGCAACGAGCGCAAC

CCTTATGGTCAGTTACTACGCAAGAGGACTCTGGCCAGACTGCCGTTG

ACAAAACGGAGGAAGGTGGGGATGACGTCAAATCATCATGCCCTTTAT

GACTTGGGCTACACACGTACTACAATGGCGTTAAACAAAGAGAAGCAA

GACCGCGAGGTGGAGCAAAACTCAGAAACAACGTCCCAGTTCGGACTG

CAGGCTGCAACTCGCCTGCACGAAGTCGGAATTGCTAGTAATCGTGGA

TCAGCATGCCACGGTGAATACGTTCCCGGGCCTTGTACACACCGCCCG

TCACACCATGAGAGCCGGGGGGACCCGAAGTCGGTAGTCTAACCGCAA

GGAGGACGCCGCCGAAGGTAAAACTGGTGATTGGGGTGAAGTCGTAAC

AAG

SEQ ID No: 13: 16S rRNA sequence of
F. prausnitzii CNCM I-4575
ATCGAGTGGCGAACGGGTGAGTAACGCGTGAGGAACCTGCCTCAAAGA
GGGGGACAACAGTTGGAAACGACTGCTAATACCGCATAAGCCCACGGC
TCGGCATCGAGCAGAGGGAAAAGGAGCAATCCGCTTTGAGATGGCCTC
GCGTCCGATTAGCTAGTTGGTGAGGTAATGGCCCACCAAGGCGACGAT
CGGTAGCCGGACTGAGAGGTTAACGGCCACATTGGGACTGAGACACG
GCCCAGACTCCTACGGGAGGCAGCAGTGGGGAATATTGCACAATGGGG
GAAACCCTGATGCAGCGACGCCGCGTGGAGGAAGAAGGTCTTCGGATT
GTAAACTCCTGTTGTTGAGGAAGATAATGACGGTACTCAACAAGGAAG
TGACGGCTAACTACGTGCCAGCAGCCGCGGTAAAACGTAGGTCACAAG
CGTTGTCCGGAATTACTGGGTGTAAAGGGAGCGCAGGCGGGCGATCAA
GTTGGAAGTGAAATCCATGGGCTCAACCCATGAACTGCTTTCAAAACT
GATTGTCTTGAGTAGTGCAGAGGTAGGCGGAATTCCCGGTGTAGCGGT
GGAATGCGTAGATATCGGGAGGAACACCAGTGGCGAAGGCGGCCTACT
GGGCACCAACTGACGCTGAGGCTCGAAAGTGTGGGTAGCAAACAGGAT
TAGATACCCTGGTAGTCCACACCGTAAACGATGATTACTAGGTGTTGG
AGGATTGACCCCTTCAGTGCCGCAGTTAACACAATAAGTAATCCACCT
GGGGAGTACGACCGCAAGGTTGAAACTCAAAGGAATTGACGGGGGCCC
GCACAAGCAGTGGAGTATGTGGTTTAATTCGACGCAACGCGAAGAACC
TTACCAAGTCTTGACATCCTGCGACGATGCTAGAAATAGTATTTTCCT
TCGGGACGCAGAGACAGGTGGTGCATGGTTGTCGTCAGCTCGTGTCGT
GAGATGTTGGGTTAAGTCCCGCAACGAGCGCAACCCTTATGGTCAGTT
ACTACGCAAGAGGACTCTGGCCAGACTGCCGTTGACAAAACGGAGGAA
GGTGGGGATGACGTCAAATCATCATGCCCTTTATGACTTGGGCTACAC
ACGTACTACAATGGCGTTAAACAAAGAGAAGCAAGACCGCGAGGTGGA
GCAAAACTCAGAAACAACGTCCCAGTTCGGACTGCAGGCTGCAACTCG
CCTGCACGAAGTCGGAATTGCTAGTAATCGCAGATCAGCATGCTGCGG
TGAATACGTTCCCGGGCCTTGTACACACCGCCCGTCACACCATGAGAG
CCGGGGGACCCGAAGTCGGTAGTCTAACCGCAAGGAGGACGCCGCCG
AAGGTAAAACTGGTGATTGGGGTGAAGTCGTAACAAGGTAGCCGTC SEQ ID No: 14: 16S rRNA sequence of
F. prausnitzii CNCM I-4573
GAGAGAGCTTGCTTTCTCAAGCGAGTGGCGAACGGGTGAGTAACGCGT
GAGGAACCTGCCTCAAAGAGGGGGACAACAGTTGGAAACGACTGCTAA
TACCGCATAAGCCCACGACCCGGCATCGGGTAGAGGGAAAAGGAGCAA
TCCGCTTTGAGATGGCCTCGCGTCCGATTAGCTAGTTGGTGAGGTAAC
GGCCCACCAAGGCGACGATCGGTAGCCGGACTGAGAGGTTGAACGGCC
ACATTGGGACTGAGACACGGCCCAGACTCCTACGGGAGGCAGCAGTGG
GGAATATTGCACAATGGGGGAAACCCTGATGCAGCGACGCCGCGTGGA
GGAAGAAGGTCTTCGGATTGTAAACTCCTGTTGTTGAGGAAGATAATG
ACGGTACTCAACAAGGAAGTGACGGCTAACTACGTGCCAGCAGCCGCG
GTAAAACGTAGGTCACAAGCGTTGTCCGGAATTACTGGGTGTAAAGGG
AGCGCAGGCGGGAAGAC
AAGTTGGAAGTGAAATCCATGGGCTCAACCC
ATGAACTGCTTTCAAAACTGTTTTTCTTGAGTAGTGCAGAGGTAGGCG
GAATTCCCGGTGTAGCGGTGGAATGCGTAGATATCGGGAGGAACACCA
GTGGCGAAGGCGGCCTACTGGGCACCAACTGACGCTGAGGCTCGAAAG
TGTGGGTAGCAAACAGGATTAGATACCCTGGTAGTCCACACTGTAAAC
GATGATTACTAGGTGTTGGAGGATTGACCCCTTCAGTGCCGCAGTTAA
CACAATAAGTAATCCACCTGGGGAGTACGACCGCAAGGTTGAAACTCA
AAGGAATTGACGGGGCCCGCACAAGCAGTGGAGTATGTGGTTTAATT
CGACGCAACGCGAAGAACCTTACCAAGTCTTGACATCCTGCGACGGTG
CTGGAAACAGTGCTTTCCTTCGGGACGCAGAGACAGGTGGTGCATGGT
TGTCGTCAGCTCGTGTCGTGAGATGTTGGGTTAAGTCCCGCAACGAGC
GCAACCCTTATGGTCAGTTACTACGCAAGAGGACTCTGGCCAGACTGC
CGTTGACAAAACGGAGGAAGGTGGGGATGACGTCAAATCATCATGCCC
TTTATGACTTGGGCTACACACGTACTACAATGGCGTTAAACAAAGAGA
AGCAAGACCGCGAGGTGGAGCAAAACTCAGAAACAACGTCCCAGTTCG
GACTGCAGGCTGCAACTCGCCTGCACGAAGTCGGAATTGCTAGTAATC
GCAGATCAGCATGCTGCGGTGAATACGTTCCCGGGCCTTGTACACACC
GCCCGTCACACCATGAGAGCCGGGGGACCCGAAGTCGGTAGTCTAAC
CGCAAGGAGGACGCCGCCGAAGGTAAAACTGGTGATTGGGGTGAAGTC
GTAACAAG SEQ ID No: 15: 16S rRNA sequence of
F. prausnitzii CNCM I-4546
CAAGCGAGTGGCGAACGGGTGAGTAACGCGTGAGGAACCTGCCTCAAA
GAGGGGGACAACAGTTGGAAACGACTGCTAATACCGCATAAGCCCACG
ACCCGGCATCGGGTAGAGGGAAAAGGAGCAATCCGCTTTGAGATGGCC
TCGCGTCCGATTAGCTAGTTGGTGAGGTAACGGCCCACCAAGGCGACG
ATCGGTAGCCGGACTGAGAGGTTGAACGGCCACATTGGGACTGAGACA
CGGCCCAGACTCCTACGGGAGGCAGCAGTGGGGAATATTGCACAATGG
GGGAAACCCTGATGCAGCGACGCCGCGTGGAGGAAGAAGGTCTTCGGA
TTGTAAACTCCTGTTGTTGAGGAAGATAATGACGGTACTCAACAAGGA
AGTGACGGCTAACTACGTGCCAGCAGCCGCGGTAAAACGTAGGTCACA
AGCGTTGTCCGGAATTACTGGGTGTAAAGGGAGCGCAGGCGGGAAGAC
AAGTTGGAAGTGAAATCCATGGGCTCAACCCATGAACTGCTTTCAAAA
CTGTTTTTCTTGAGTAGTGCAGAGGTAGGCGGAATTCCCGGTGTAGCG
GTGGAATGCGTAGATATCGGGAGGAACACCAGTGGCGAAGGCGGCCTA
CTGGGCACCAACTGACGCTGAGGCTCGAAAGTGTGGGTAGCAAACAGG
ATTAGATACCCTGGTAGTCCACACTGTAAACGATGATTACTAGGTGTT
GGAGGATTGACCCCTTCAGTGCCGCAGTTAACACAATAAGTAATCCAC
CTGGGGAGTACGACCGCAAGGTTGAAACTCAAAGGAATTGACGGGGC
CCGCACAAGCAGTGGAGTATGTGGTTTAATTCGACGCAACGCGAAGAA
CCTTACCAAGTCTTGACATCCTGCGACGCACATAGAAATATGTGTTTC

```
CTTCGGGACGCAGAGACAGGTGGTGCATGGTTGTCGTCAGCTCGTGTC
GTGAGATGTTGGGTTAAGTCCCGCAACGAGCGCAACCCTTATGGTCAG
TTACTACGCAAGAGGACTCTGGCCAGACTGCCGTTGACAAAACGGAGG
AAGGTGGGGATGACGTCAAATCATCATGCCCTTTATGACTTGGGCTAC
ACACGTACTACAATGGCGTTAAACAAAGAGAAGCAAGACCGCGAGGTG
GAGCAAAACTCAGAAACAACGTCCCAGTTCGGACTGCAGGCTGCAACT
CGCCTGCACGAAGTCGGAATTGCTAGTAATCGCAGATCAGCATGCTGC
GGTGAATACGTTCCCGGGCCTTGTACACACCGCCCGTCACACCATGAG
AGCCGGGGGACCCGAAGTCGGTAGTCTAACCGCAAGGAGGACGCCGC
CGAAGGTAAAACTGGTGATTGGGGTGAAGTCGTAACAAGGGTAG
```

SEQ ID No: 16: 16S rRNA sequence of
F. prausnitzii CNCM I-4541
```
AGAGTTTGATCCTGGCTCAGGACGAACGCTGGCGGCGCGCCTAACACA
TGCAAGTCGAACGAGCGAGAGAGAGCTTGCTTTCTCGAGCGAGTGGCG
AACGGGTGAGTAACGCGTGAGGAACCTGCCTCAAAGAGGGGGACAACA
GTTGGAAACGACTGCTAATACCGCATAAGCCCACGACCCGGCATCGGG
TTGAGGGAAAAGGAGCAATCCGCTTTGAGATGGCCTCGCGTCCGATTA
GCTAGTTGGTGAGGTAACGGCCCACCAAGGCGACGATCGGTAGCCGGA
CTGAGAGGTTGAACGGCCACATTGGGACTGAGACACGGCCCAGACTCC
TACGGGAGGCAGCAGTGGGGAATATTGCACAATGGGGGAAACCCTGAT
GCAGCGACGCCGCGTGGAGGAAGAAGGTCTTCGGATTGTAAACTCCTG
TTGTTGGGGAAGATAATGACGGTACCCAACAAGGAAGTGACGGCTAAC
TACGTGCCAGCAGCCGCGGTAAAACGTAGGTCACAAGCGTTGTCCGGA
ATTACTGGGTGTAAAGGGAGCGCAGGCGGGAAGACAAGTTGGAAGTGA
AATCCATGGGCTTAACCCATGAACTGCTTTCAAAACTGTTTTTCTTGA
GTAGTGCAGAGGTAGGCGGAATTCCCGGTGTAGCGGTGGAATGCGTAG
ATATCGGGAGGAACACCAGTGGCGAAGGCGGCCTACTGGGCACCAACT
GACGCTGAGGCTCGAAAGTGTGGGTAGCAAACAGGATTAGATACCCTG
GTAGTCCACACCGTAAACGATGATTACTAGGTGTTGGAGGATTGACCC
CTTCAGTGCCGCAGTTAACACAATAAGTAATCCACCTGGGGAGTACGA
CCGCAAGGTTGAAACTCAAAGGAATTGACGGGGGCCCGCACAAGCAGT
GGAGTATGTGGTTTAATTCGACGCAACGCGAAGAACCTTACCAAGTCT
TGACATCCTGTGACAGACGTAGAAATACGTTCTTCCTTCGGGACACAG
AGACAGGTGGTGCATGGTTGTCGTCAGCTCGTGTCGTGAGATGTTGGG
TTAAGTCCCGCAACGAGCGCAACCCTTATGGTCAGTTACTACGCAAGA
GGACTCTGGCCAGACTGCCGTTGACAAAACGGAGGAAGGTGGGGATGA
CGTCAAATCATCATGCCCTTTATGACTTGGGCTACACACGTACTACAA
TGGCGTTAAACAAAGAGAAGCAAGACCGCGAGGTGGAGCAAAACTCAG
AAACAACGTCCCAGTTCGGACTGCAGGCTGCAACTCGCCTGCACGAAG
TCGGAATTGCTAGTAATCGTGGATCAGCATGCCACGGTGAATACGTTC
```

```
CCGGGCCTTGTACACACCGCCCGTCACACCATGAGAGCCGGGGGACCC
CGAAGTCGGTAGTCTAACCGCAAGGAGGACGCCGCCGAAGGTAAAACT
GGTGATTGGGGTGAAGTCGTAACAAGGTAGCCGT
```

SEQ ID No: 17: 16S rRNA sequence of
F. prausnitzii S13E3
```
TTAGTGGCGAACGGGTGAGTAACGCGTGAGTAACCTGCCCTGGAGTGG
GGGACAACAGTTGGAAACGACTGCTAATACCGCATAAGCCCACGGCCC
GGCATCGGGCTGCGGGAAAAGGATTTATTCGCTTCAGGATGGACTCGC
GTCCAATTAGCTAGTTGGTGAGGTAACGGCCCACCAAGGCGACGATTG
GTAGCCGGACTGAGAGGTTGAACGGCCACATTGGGACTGAGACACGGC
CCAGACTCCTACGGGAGGCAGCAGTGGGGATATTGCACAATGGGGGA
AACCCTGATGCAGCGACGCCGCGTGGAGGAAGAAGGTTTTCGGATTGT
AAACTCCTGTCGTTAGGGACGAATCATGACGGTACCTAACAAGAAAGC
ACCGGCTAACTACGTGCCAGCAGCCGCGGTAAAACGTAGGGTGCAAGC
GTTGTCCGGAATTACTGGGTGTAAAGGGAGCGCAGGCGGACCGGCAAG
TTGGAAGTGAAAACCATGGGCTCAACCCATGAATTGCTTTCAAAACTG
CTGGCCTTGAGTAGTGCAGAGGTAGGTGGAATTCCCGGTGTAGCGGTG
GAATGCGTAGATATCGGGAGGAACACCAGTGGCGAAGGCGACCTACTG
GCACCAACTGACGCTGAGGCTCGAAAGCATGGGTAGCAAACAGGATT
AGATACCCTGGTAGTCCATGCCGTAAACGATGATTACTAGGTGTTGGA
GGATTGACCCCTTCAGTGCCGCAGTTAACACAATAAGTAATCCACCTG
GGGAGTACGACCGCAAGGTTGAAACTCAAAGGAATTGACGGGGGCCCG
CACAAGCAGTGGAGTATGTGGTTTAATTCGAAGCAACGCGAAGAACCT
TACCAGGTCTTGACATCCGATGCATAGTGCAGAGATGCATGAAGTCCT
TCGGGACATCGAGACAGGTGGTGCATGGTTGTCGTCAGCTCGTGTCGT
GAGATGTTGGGTTAAGTCCCGCAACGAGCGCAACCCTTATTGCCAGTT
ACTACGTAAGAGGACTCTGGCGAGACTGCCGTTGACAAAACGGAGGAA
GGTGGGGATGACGTCAAATCATCATGCCCTTTATGACCTGGGCTACAC
ACGTACTACAATGGCGTTTAACAAAGAGAAGCAAGACCGCGAGGTGGA
GCAAAACTCAGAAACAACGTCTCAGTTCAGATTGCAGGCTGCAACTCG
CCTGCATGAAGTCGGAATTGCTAGTAATCGCGGATCAGCATGCCGCGG
TGAATACGTTCCCGGGCCTTGTACACACCGCCCGTCACACCATGAGAG
CCGGGGGGACCCGAAGTCGGTAGTCTA
```

SEQ ID No: 18: 16S rRNA sequence of
Eubacterium desmolans ATCC 43058
```
TTTTTAGAGAGTTTGATCCTGGCTCAGGATAACGCTGGCGGCGTGCC
TAACACATGCAAGTCGAACGGAGTTATTTTGGAAATCTCTTCGGAGAT
GGAATTCATAACTTAGTGGCGGACGGGTGAGTAACGCGTGAGCAATCT
GCCTTTAGGTGGGGGATAACAGTCGGAAACGGCTGCTAATACCGCATA
ATACGTTTTGGGGCATCCTTGAAACGTCAAAGATTTATTGCCTTTAG
ATGAGCTCGCGTCTGATTAGCTGGTTGGCGGGGNAACGGCCCACCAAG
GCGACGATCAGTAGCCGGACTGAGAGGTTGAACGGCCACATTGGGACT
GAGACACGGCCCAGACTCCTACGGGAGGCAGCAGTGGGGAATATTGCG
```

CAATGGGGGAAACCCNGACGCAGCAACGCCGCGTGATTGAAGAAGGCC

TTCGGGTTGTAAAGATCTTTAATCAGGGACGAATTTTGACGGTACCTG

AAGAATAAGCTCCGGCTAACTACGTGCCAGCAGCCGCGGTAATACGTA

GGGAGCAAGCGTTATCCGGATTTACTGGGTGTAAAGGGCGCGCAGNCG

GGNCGGCAAGTTGGGAGTGAAATCNGGGGGCTTAACCCCCGAACTGCT

TTCAAAACTGCTGGTCTTGAGTGATGGAGAGGCAGGCGGAATTCCGTG

TGTAGCGGTGAAATGCGTAGATATACGGAGGAACACCAGTGGCGAAGG

CGGCCTGCTGGACATTAACTGACGCTGAGGCGCGAAAGCGTGGGGAGC

AAACAGGATTAGATACCCTGGTAGTCCACGCCGTAAACGATGGATACT

AGGTGTGGGAGGTATTGACCCCTTCCGTGCCGCAGTTAACACAATAAG

TATCCCACCTGGGGAGTACGGCCGCAAGGTTGAAACTCAAAGGAATTG

ACGNNNGCCCGCACAAGCAGTGGAGTATGTGGTTTAATTCGAANNAAC

GCGAAGAACCTTACCAGGNCTTGACATCCCGGTGACCGTCCTAGAGAT

AGGACTTNCCTTCGGGNCAACGGTGACAGNTGGTGCATGGTTGTCGTC

AGCTCGTGTCGTGAGATGTTGGNTTAAGTCCCGCAACGAGCGCAACCC

TTACGGTTAGTTGATACGCAAGATCACTCTAGCCGGACTGCCGTTGAC

AAAACGGAGGAAGGTGGGGACGACGTNNAATCATCATGCCCCNTATGA

CCTGGGCTACACACGTACTACAATGGCAGTCATACAGAGGGAAGCAAA

ATCGCGAGGTGGAGCAAATCCCTAAAAGCTGTCCCAGTTCAGATTGCA

GGCTGCAACCCGCCTGCATGAAGTCGGAATTGCTAGTAATCGCGGATC

AGCATGCCGCGGTGAATACGTTCCCGGGNNTTGTACACACCGCCCGTC

ACACCATGAGAGCCGTCAATACCCGAAGTCCGTAGCCTAACCGCAAGG

GGGGCGCGGCCGAAGGTAGGGGTGGTAAT

The invention claimed is:

1. Method for the treatment of visceral abdominal pain in an individual, comprising administering to said individual a bacterial strain of the Faecalibacteriunm *prausnitzii* species, the bacterial strain being the strain deposited to the CNCM under the accession number I-4573.

2. The method according to claim 1, wherein the visceral abdominal pain is a gastrointestinal pain.

3. The method according to claim 1, wherein the visceral abdominal pain is caused by a gastrointestinal disorder.

4. The method according to claim 3, wherein the gastrointestinal disorder is a gastrointestinal hypersensitivity.

5. The method according to claim 1, wherein the bacterial strain is comprised in a composition comprising a physiologically acceptable medium.

* * * * *